(12) United States Patent
Izatt et al.

(10) Patent No.: US 8,718,743 B2
(45) Date of Patent: May 6, 2014

(54) METHODS FOR SINGLE-PASS VOLUMETRIC BIDIRECTIONAL BLOOD FLOW IMAGING SPECTRAL DOMAIN OPTICAL COHERENCE TOMOGRAPHY USING A MODIFIED HILBERT TRANSFORM

(75) Inventors: Joseph A. Izatt, Raleigh, NC (US); Yuankai K. Tao, Durham, NC (US); Anjul M. Davis, Little Falls, NJ (US)

(73) Assignee: Duke University, Durham, NC (US)

( * ) Notice: Subject to any disclaimer, the term of this patent is extended or adjusted under 35 U.S.C. 154(b) by 330 days.

(21) Appl. No.: 12/386,945

(22) Filed: Apr. 24, 2009

(65) Prior Publication Data

US 2009/0270738 A1    Oct. 29, 2009

Related U.S. Application Data

(60) Provisional application No. 61/047,518, filed on Apr. 24, 2008.

(51) Int. Cl.
  *A61B 5/00* (2006.01)
(52) U.S. Cl.
  USPC ........... 600/407; 600/473; 600/479; 356/450; 356/477; 702/190; 351/205
(58) Field of Classification Search
  USPC .......... 600/476, 477, 479, 310, 504; 356/450, 356/451, 477
  See application file for complete search history.

(56) References Cited

U.S. PATENT DOCUMENTS

| | | | |
|---|---|---|---|
| 4,052,889 A * | 10/1977 | Mucciardi et al. | ............... 73/602 |
| 5,491,524 A | 2/1996 | Hellmuth et al. | |
| 5,588,435 A | 12/1996 | Weng et al. | |
| 5,994,690 A | 11/1999 | Kulkarni et al. | |
| 6,618,152 B2 | 9/2003 | Toida | |
| 6,887,231 B2 | 5/2005 | Mrochen et al. | |
| 6,940,557 B2 | 9/2005 | Handjojo et al. | |
| 7,092,748 B2 | 8/2006 | Valdes Sosa et al. | |
| 7,102,756 B2 | 9/2006 | Izatt et al. | |
| 7,187,800 B2 | 3/2007 | Hibbard | |
| 7,330,270 B2 | 2/2008 | O'Hara et al. | |
| 7,486,406 B2 | 2/2009 | Kim | |
| 7,602,500 B2 | 10/2009 | Izatt | |

(Continued)

FOREIGN PATENT DOCUMENTS

| | | |
|---|---|---|
| EP | 2427723 | 3/2012 |
| WO | WO 2010-129544 | 11/2010 |

OTHER PUBLICATIONS

Three dimensional optical angiography. Wang et al. Optics Express vol. 15, No. 7 (Apr. 2, 2007) 4083-4097.*

(Continued)

*Primary Examiner* — Unsu Jung
*Assistant Examiner* — Phong K Huynh
(74) *Attorney, Agent, or Firm* — Jenkins, Wilson, Taylor & Hunt, P.A.

(57) ABSTRACT

The present subject matter relates to in vivo volumetric bidirectional blood flow imaging using single-pass flow imaging spectral domain optical coherence tomography. This technique uses a modified Hilbert transform algorithm to separate moving and non-moving scatterers within a depth. The resulting reconstructed image maps the components of moving scatterers flowing into and out of the imaging axis onto opposite image halfplanes, enabling volumetric bidirectional flow mapping without manual segmentation.

22 Claims, 13 Drawing Sheets

(7 of 13 Drawing Sheet(s) Filed in Color)

(56) References Cited

U.S. PATENT DOCUMENTS

| | | | |
|---|---|---|---|
| 7,648,242 | B2 | 1/2010 | Ferguson et al. |
| 7,719,692 | B2 | 5/2010 | Izatt |
| 7,796,243 | B2 | 9/2010 | Choo-Smith et al. |
| 7,907,765 | B2 | 3/2011 | Fauver et al. |
| 7,990,541 | B2 | 8/2011 | Izatt |
| 8,149,418 | B2 | 4/2012 | Tearney et al. |
| 8,155,420 | B2 | 4/2012 | Meyer et al. |
| 8,565,499 | B2 | 10/2013 | Zhao et al. |
| 2005/0057756 | A1 | 3/2005 | Fang-Yen et al. |
| 2005/0171438 | A1 | 8/2005 | Chen et al. |
| 2007/0258094 | A1 | 11/2007 | Izatt et al. |
| 2008/0309881 | A1 | 12/2008 | Huang et al. |
| 2009/0185166 | A1* | 7/2009 | Oldenburg et al. ............. 356/72 |
| 2009/0257636 | A1 | 10/2009 | Wei et al. |
| 2010/0150467 | A1 | 6/2010 | Zhao |
| 2011/0007321 | A1 | 1/2011 | Everett et al. |
| 2011/0032533 | A1 | 2/2011 | Izatt |
| 2012/0188555 | A1 | 7/2012 | Izatt |

OTHER PUBLICATIONS

Three-dimensional optical micro-angiography maps directional blood perfusion deep within microcirculation tissue beds in vivo. Wang, Ruikang K. Phys. Med. Biol. 52 (Nov. 6, 2007) N531-N537.*
Ding et al. "Real-time phase-resolved optical coherence tomography and optical Doppler tomography". Optics Express vol. 10 No. 5, Mar. 11, 2002.*
Yogesh Verma et al, "Use of common path phase sensitive spectral domain optical coherence tomography for refractive index measurements." Applied Optics, 2011, pp. E7-E12, vol. 50, Issue 25.
Park et al, "Double common-path interferometer for flexible optical probe of optical coherence tomography." Optics Express, 2012, pp. 1102-1112, vol. 20, Issue 2.
Liu et al, "Compressive SD-OCT: the application of compressed sensing in spectral domain optical coherence tomography." Optics Express, 2010, pp. 22010-22019, vol. 18, Issue 21.
Vergnole et al, "Common Path swept source OCT interferometer with artifact removal." Proc of SPIE, 2008, 8 pages, vol. 6847.
Jae Ho Han et al, "Common path fourier domain optical coherence tomography in ophthalmology applications." Life Science Systems and Applications Workshop, 2009, pp. 163-166.
O. W. Richards, "Phase Difference Microscopy," Nature, 1944, vol. 154, No. 672.
C. R. Tilford, "Analytical procedure for determining lengths from fractional fringes," Appl. Opt. 16, 1977, pp. 1857-1860.
Y. Cheng and J. C. Wyant, "Two-wavelength phase shifting interferometry," Appl. Opt. 23, 1984, pp. 4539-4543.
K. Creath, "Phase-shifting speckle interferometry," Appl. Opt. 24, 1985, pp. 3053-3058.
H. Gundlach, "Phase contrast and differential interference contrast instrumentation and applications in cell, developmental, and marine biology," Opt. Eng. 32, 1993, pp. 3223-3228.
E. Cliche, F. Bevilacqua, and C. Depeursinge, "Digital Holography for quantitative phase-contrast imaging," Opt. Lett. 24, 1999, pp. 291-293.
C.K. Hitzenberger, M. Sticker, R. Leitgeb, and A.F. Fercher, "Differential phase measurements in low-coherence interferometry without $2\pi$ ambiguity," Opt. Lett. 26, 2001, pp. 1864-1866.
Hirwnvwefwe et al., "Overcoming the 2it ambiguity in low coherence interferometric differential phase measurements," Proc. SPIE, Coherence Domain Optical Methods in Biomedical Science and Clinical Apolicatiom 2001, vol. 4251 pp. 81-85.
C. Yang, A. Wax, R.R. Dasari, and M.S. Feld, "$2\pi$ ambiguity-free optical distance measurement with subnanometer precision with a novel phase-crossing low-coherence interferometer," Opt. Lett. 27, 2002, pp. 77-79.
D.R. Lide, ed., "CRC Handbook of Chemistry and Physics," CRC Press, 2001-2002.
R. Tripathi, N Nassif, J. S. Nelson, B. H. Park, and J. F. De Boer, "Spectral shaping for non-Gaussian source spectra in optical coherence tomography," Opt. Lett. 27, 2002, pp. 406-408.
Westphal, Volker et al., "Correction of Geometric and Refractive Image Distortions in Optical Coherence Tomography Applying Fermat's Principle," Optics Express, May 6, 2002, pp. 397-404, vol. 10, No. 9.
J. Gass, A. Dakoff, and M. K. Kim, "Phase imaging without $2\pi$ ambiguity by multiwavelength digital holography," Opt. Lett. 28, 2003, pp. 1141-1143.
J.F. De Boer, B. Cense, B. H. Park, M. C. Pierce, G. J. Tearney, and B. E. Bouma, "Improved signal-to-noise ratio in spectral-domain compared with time-domain optical coherence tomography," Opt. Lett. 28, 2003, pp. 2067-2069.
M. A. Choma, M. V. Sarunic, C. Yang, and J. A. Izatt, "Sensitivity advantage of swept source and Fourier domain optical coherence tomography," Opt. Express 11, 2003, pp. 2183-2189.
R. Leitgeb, C. K. Hitzenberger, and A. F. Fercher, "Performance of Fourier domain vs. time domain optical coherence tomography," Opt. Express 11, 2003, pp. 889-894.
Zawadzki, Robert J. et al., "Three-Dimensional Ophthalmic Optical Coherence Tomography With a Refraction Correction Algorithm," SPIE, 2003, vol. 5140.
D.L. Marks, P.S. Carney, and S.A. Boppart, "Adaptive spectral apodization for sidelobe reduction in optical coherence tomography images," J. Biomed. Opt. 9, 2004, pp. 1281-1287.
G. Popescu, L. P. Deflores, J.C. Vaughan, K. Badizadegan, H. Iwai, R. R. Dasari, and M. S. Feld, "Fourier phase microscopy for investigation of biological structures and dynamics," Opt. Lett. 29, 2004, pp. 2503-2505.
Tang, Maolong, "Corneal Mean Curvature Mapping: Applications in Laser Refractive Surgery," Biomedical Engineering Center, 2004, Ohio State University.
Yun, S. et al., "Removing the depth-degeneracy in optical frequency domain imaging with frequency shifting," Optics Express, Oct. 4, 2004, vol. 12, No. 20.
C. Joo, T. Akkin, B. Cense, B. H. Park, and J. F. De Boer, "Spectral-domain optical coherence phase microscopy for quantitative phase-contrast imaging," Opt. Lett. 30, 2005, pp. 2131-2133.
C. J. Mann, L. Yu, C. Lo, and M. K. Kim, "High-resolution quantitative phase-contrast microscopy by digital holography," Opt. Express 13, 2005, pp. 8693-8698.
Davis, A.M. et al. "Heterodyne swept-source optical coherence tomography for complete complex conjugate ambiguity removal", Journal of Biomedical Optics, Nov./Dec. 2005, vol. 10, No. 6.
G. Popescu, T. Ikeda, C. A. Best, K. Badizadegan, R. R. Dasari, and M. S. Feld, "Erythrocyte structure and dynamics quantified by Hilbert phase microscopy," J. Biomed. Opt. 10, 2005, 060503.
M. A. Choma, A. K. Ellerbee, C. Yang, T. L. Creazzo, and J. A. Izatt, "Spectral-domain phase microscopy," Opt. Lett. 30, 2005, pp. 1162-1164.
T. Ikeda, G. Popescu, R. R. Dasari, and M.S. Feld, "Hilbert phase microscopy for investigating fast dynamics in transparent systems," Opt. Lett. 30, 2005, pp. 1165-1167.
M. A. Choma, A. K. Ellerbee, S. Yazdanfar, and J. A. Izatt, "Doppler flow imaging of cytoplasm streaming using spectral domain phase microscopy," J. Biomed. Opt. 11, 2006, 024014.
Sicam, Victor Arni D.P., "Spherical Aberration of the Anterior and Posterior Surfaces of the Human Cornea," J. Opt. Soc. Am. A, Mar. 2006, pp. 544-549, vol. 23, No. 3.
Tang, Maolong et al., "Measuring Total Corneal Power Before and After Laser in Situ Keratomileusis With High-Speed Optical Coherence Tomography," J. Cataract Refract Surg, Nov. 2006, pp. 1843-1850, vol. 32, No. 11.
A. K. Ellerbee and J.A. Izatt, "Phase retrieval in low-coherence interferometric microscopy," Opt. Lett. 32, 2007, pp. 388-390.
A. K. Ellerbee, T. L. Creazzo, and J. A. Izatt, "Investigating nanoscale cellular dynamics with cross-sectional spectral domain phase microscopy," Opt. Express 15, 2007, pp. 8115-8124.
E. J. McDowell, A. K. Ellerbee, M. A. Choma, B. E. Applegate, and J. A. Izatt, "Spectral domain phase microscopy for local measurements of cytoskeletal rheology in single cells", J. Biomed. Opt., 2007, 04400.
J. Kuhn, T. Colomb, F. Montfort, F. Charrière, Y. Emery, E. Cuche, P. Marquet, and C. Depeursinge, "Real-time dual-wavelength digital

(56) References Cited

OTHER PUBLICATIONS holographic microscopy with a single hologram acquisition," Opt. Express 15, 2007, pp. 7231-7242.

N. Warnasooriya and M.K. Kim, "LED-based multi-wavelength phase imaging interference microscopy," Opt. Express 15, 2007, pp. 9239-9247.

N. Lue W. Choi, G. Popescu, T. Ikeda, R. R. Dasari, K Badizadegan, and M. S. Feld, "Quantitative phase imaging of live cells using fast Fourier phase microscopy," Appl. Opt. 46, 2007, pp. 1836-1842.

A. Khmaladze, A. Restrepo-Martínez, M.K. Kim, R. Castañeda, and A. Blandón, "Simultaneous Dual-Wavelength Reflection Digital Holography Applied to the Study of the Porous Coal Samples," Appl. Opt. 47, 2008, pp. 3203-3210.

D. L. Marks, S.C. Schlachter, A.M. Zysk, and S.A. Boppart, "Group refractive index reconstruction with broadband interferometric confocal microscopy," J. Opt. Soc. Am. A 25, 2008, pp. 1156-1164.

Erich Götzinger, Michael Pircher, Wolfgang Geitzenauer, Christian Ahlers, Bernhard Baumann, Stephan Michels, Ursula Schmidt-Erfurth, and Christoph K. Hitzenberger, "Retinal pigment epithelium segmentation by polarization sensitive optical coherence tomography," Opt. Express.

J.A. Izatt and M.A. Choma, "Theory of Optical Coherence Tomography," in Optical Coherence Tomography: Technology and Applications, W. Drexler and J.G. Fujimoto, eds, Springer, 2008.

R. M. Werkmeister, N. Dragostinoff, M. Pircher, E. Götzinger, C. K. Hitzenberger, R. A. Leitgeb, and L. Schmetterer, "Bidirectional Doppler Fourier-domain optical coherence tomography for measurement of absolute flow velocities in human retinal vessels," Opt. Lett. 33, 2008, pp. 2967-2969.

S. Tamano et al., "Phase-shifting digital holography with a low-coherence light source for reconstruction of a digital relief object hidden behind a light-scattering medium," Applied Optics, 2008, pp. 953-959, vol. 45, No. 5, Optical Society of America.

Sarunic, Marinko et al., "Imaging the Ocular Anterior Segment With Real-Time, Full-Range Fourier-Domain Optical Coherence Tomography," Arch. Opthal., Apr. 2008, pp. 537-542, vol. 126, No. 4.

V. Srinivasan, B.K. Monson, M. Wojtkowski, R.A. Bilonick, I. Gorczynksa, R. Chen, J.S. Duker, J.S. Schumann, J.G. Fujimoto, "Characterization of Outer Retinal Morphology with High-Speed, Ultrahigh Resolution Optical Coherence Tomography," Investigative Ophthalmology and Visual Science 49,2008, pp. 1571-.

H.C. Hendargo, M. Zhao, N. Shepard, and J.A. Izatt, "Synthetic wavelength based phase unwrapping in spectral domain optical coherence tomography," Opt. Express 17, 2009, pp. 5039-5051.

Hendargo et al., "Synthetic Wavelength-Based Phase Unwrapping in Fourier Domain Optical Coherence Tomography," Optics Express, 2009, pp. 5039-5051, vol. 17, Issue 7. http://dx.doi.org/10.1364/OE.17.005039.

Zhao, Mingtao et al., "Single-Camera Sequential-Scan-Based Polarization-Sensitive SDOCT for Retinal Imaging," Optics Letters, Jan. 15, 2009, pp. 205-207, vol. 34, No. 2.

International Search Report and Written Opinion for Application No. PCT/US2010/033540 dated Jul. 16, 2010.

Wieserlabs Ug Data Sheet—1 GHz Dual-Balanced InGaAs Low Noise Photodetector No. WL-BPD1GA, www.wieserlabs.com, Oct. 2011.

Non-Final Office Action for U.S. Appl. No. 12/460,532 dated Jul. 13, 2012.

Notice of Allowance for U.S. Appl. No. 12/460,532 dated Feb. 20, 2013.

Notice of Allowance for U.S. Appl. No. 12/460,532 dated May 24, 2013.

Notice of Allowance for U.S. Appl. No. 12/799,890 dated Nov. 19, 2013.

Uhlhorn et al., "Refractive Index Measurement of the Isolated Crystalline Lens Using Optical Coherence Tomography," Vision Research 48 (2008), pp. 2732-2738.

Non-Final Office Action for U.S. Appl. No. 12/799,890 dated Aug. 9, 2013.

* cited by examiner

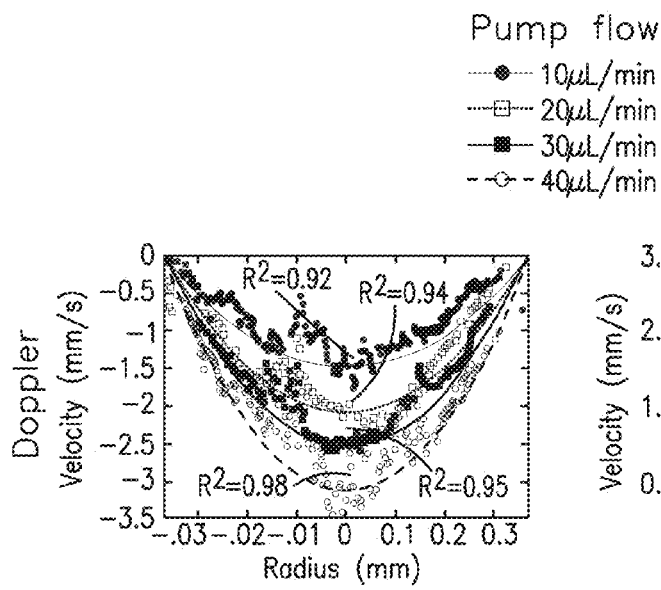
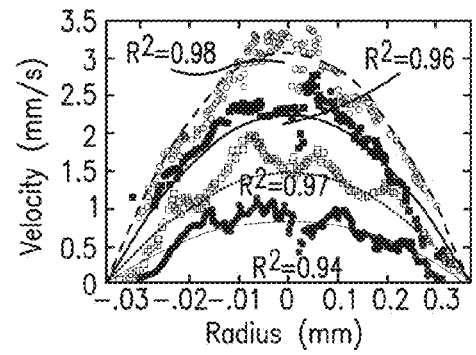
FIG. 8b     FIG. 8c
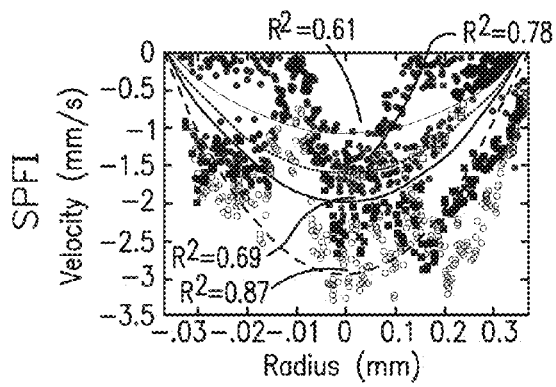
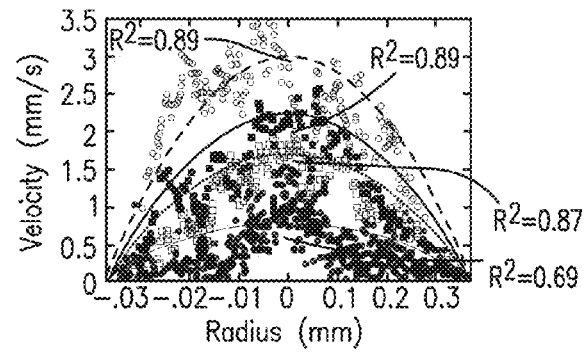
FIG. 8d     FIG. 8e
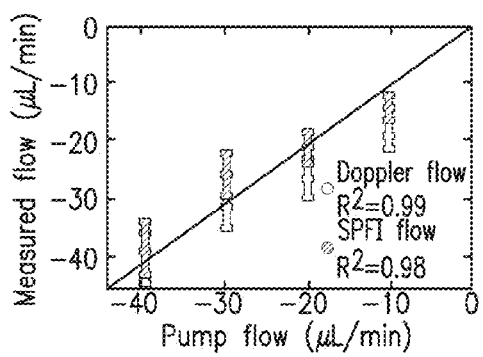
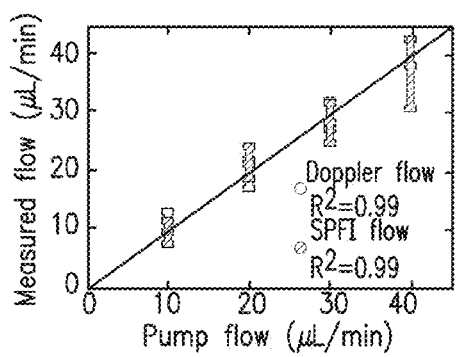
FIG. 8f     FIG. 8g

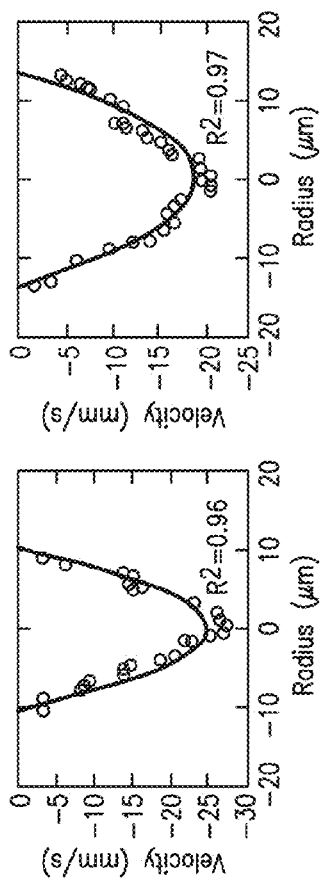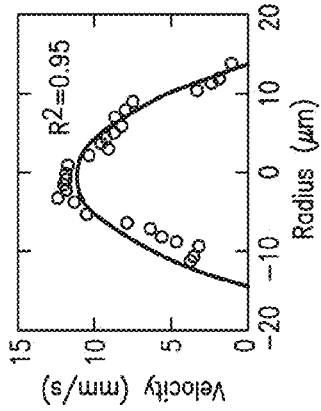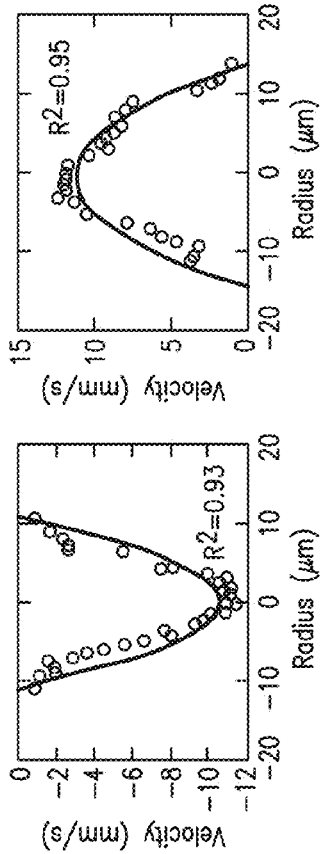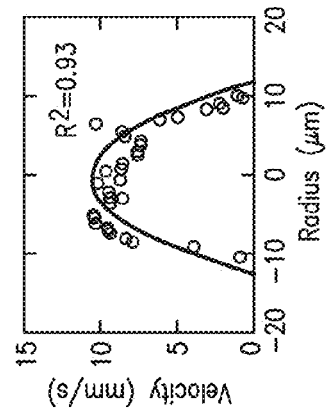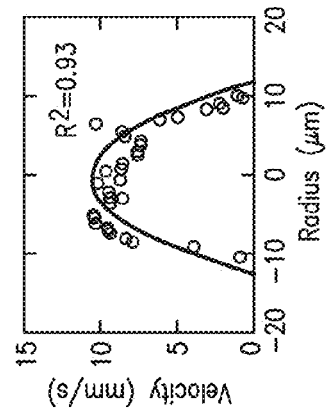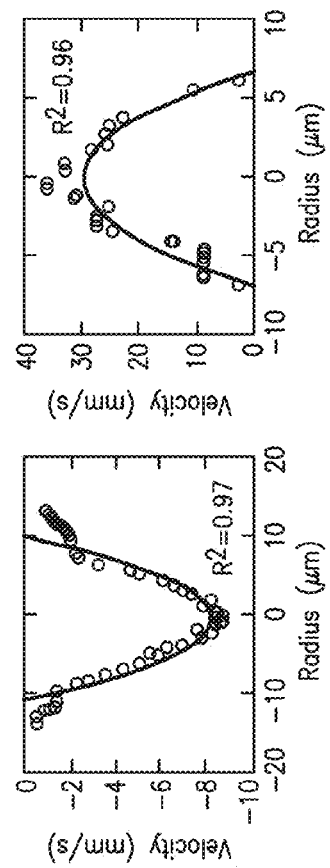
FIG. 13c  FIG. 13d  FIG. 13e  FIG. 13f  FIG. 13g  FIG. 13h  FIG. 13i

METHODS FOR SINGLE-PASS VOLUMETRIC BIDIRECTIONAL BLOOD FLOW IMAGING SPECTRAL DOMAIN OPTICAL COHERENCE TOMOGRAPHY USING A MODIFIED HILBERT TRANSFORM

RELATED APPLICATIONS

The presently disclosed subject matter claims the benefit of U.S. Provisional Patent Application Ser. No. 61/047,518, filed Apr. 24, 2008, the disclosure of which is incorporated herein by reference in its entirety.

GOVERNMENT INTEREST

This invention was made with government support under Grant No. R21-EY017393 awarded by the National Institutes of Health. The government has certain rights in the invention.

TECHNICAL FIELD

The subject matter disclosed herein relates generally to in vivo volumetric bidirectional blood flow imaging. More particularly, the subject matter disclosed herein relates to methods for imaging using spectral domain optical coherence tomography.

BACKGROUND

Spectral domain optical coherence tomography (SDOCT), including both spectrometer-based and swept-source systems, has demonstrated clinical potential for in vivo high-resolution and high-speed imaging of biological structures. Advances in Doppler SDOCT have demonstrated several image acquisition schemes that enabled real-time, high-resolution, volumetric display of blood flow maps. These techniques, while able to provide 3D flow maps and velocimetry data, are inherently oversampled and therefore have reduced imaging speed and are more susceptible to sample motion.

Current generation Doppler SDOCT techniques use phase differences between sequential A-scans acquired at a single lateral position to calculate the velocity of moving scatterers through depth. These techniques relate the phase differences between sequential interferograms to a Doppler frequency-shift which, in turn, is related to the velocity of the moving scatterers. Recently, advances in Doppler SDOCT have led to a joint spectral and time domain acquisition scheme (STdOCT), which allows for near phase-noise limited velocity resolution in low signal conditions. This technique is a variation of conventional Doppler, which functions by determining the velocity of moving scatterers using their temporal frequency shifts rather than the phase differences between sequential A-scans at a single lateral scan position. By taking a 2D Fourier transform of interference fringes temporally oversampled at the same A-scan position 20-40 times, STdOCT directly maps wave number to depth and time to Doppler frequency, thus creating a depth-resolved Doppler velocity map. This technique, while able to provide depth-resolved flow images and velocimetry data, is several times more oversampled than conventional Doppler, making it more susceptible to motion artifacts. Other techniques for identifying vessels involve injections of contrast agents such as FA and ICGA, and/or manual segmentation of vessels.

Spatial frequency modulations across lateral scans have been introduced as a method for full range complex conjugate resolved imaging. Similar to previously described complex conjugate resolving techniques using electro-optic phase modulators and acousto-optic frequency shifters, the spatial frequency modulation technique separates real and complex conjugate reflectivities by imposing a spatial carrier frequency laterally across a B-scan. The carrier frequency is generated by adding a phase delay to each A-scan using a moving reference arm or an off-pivot scanning beam. Similarly, a 3D optical angiography technique has been demonstrated by using a modulated reference arm delay and by detecting scatterers not modulated at the carrier frequency as a result of flow-induced Doppler frequency-shifts. Resonant Doppler flow imaging also uses reference arm modulations to detect flow, but instead of using a moving reference arm mirror, resonant. Doppler uses an electro-optic modulator, driven at a flow detection frequency, to phase-match the reference signal to that of the moving scatterer.

Spatial frequency flow detection techniques can be considered optical analogs to power Doppler (PD) ultrasonography. Developed as a method of improving the sensitivity of Doppler ultrasound, the analog to DOCT, PD reports the power of the Doppler signal within specified frequency windows instead of the mean frequency shift. The advantage arises from the representation of the power spectrum of random phase noise. Since the noise in the power spectrum is uniformly low, random phase variations can be filtered out by raising the sensitivity threshold above the noise floor. The Doppler signal in PD is represented as an integral of the power spectrum, which improves the sensitivity and detection range of moving scatterers at the expense of eliminating velocity information. PD is relatively insensitive to Doppler angle and phase wrapping since these factors only modify the distribution of the Doppler power spectrum, but the total integrated power remains constant. The Doppler signal in PD is separated from non-moving components by filtering out all power spectrum components without Doppler shifts, thus only imaging moving scatterers. The resulting PD signal is related to the number of moving scatterers producing the corresponding Doppler shifts.

These techniques rely on precise synchronization of reference arm modulation and B-scan acquisition, require expensive or cumbersome modulators, and are unable to detect bidirectional flow in a single B-scan pass. In addition, spatial frequency filtering techniques, while able to provide 3D flow maps with improved acquisition speed and sensitivity compared with DOCT, lack velocity-resolved blood flow information provided by techniques such as DOCT and laser Doppler velocimetry (LDV). Accordingly, in ophthalmology, noninvasive quantification of blood circulation in tissues would be advantageous to facilitate the description of retinal vascular changes prior to and during ocular and systemic disease.

SUMMARY

In accordance with this disclosure, methods for imaging using spectral domain optical coherence tomography are provided. In one aspect, a method for imaging using a spectral domain optical coherence tomographic (SDOCT) device is provided. The method can include producing interferometric signals from an SDOCT device, the interferometric signals containing moving scatterer data from non-moving scatterer data, separating the moving scatterer data from the non-moving scatterer data in the interferometric signals using a modified Hilbert transform algorithm, and producing a flow image of the moving scatterer data.

In another aspect, a method for blood flow imaging is provided. The method can include emitting a light from a light source, splitting the light into a first light and a second light, directing the first light toward a sample containing moving and non-moving scatterers within a depth to produce a first reflected light, the first reflected light containing an image of both the moving and non-moving scatterers, directing the second light toward a reference reflector to create a second reflected light, combining the first reflected light and the second reflected light to produce interferometric signals, the interferometric signals containing moving scatterer data from non-moving scatterer data, separating the moving scatterer data from the non-moving scatterer data in the interferometric signals using a modified Hilbert transform algorithm, and producing a flow image of the moving scatterer data.

It is therefore an object of the presently disclosed subject matter to provide methods that improve data acquisition speeds over DOCT for imaging of small spatial volumes of moderately high flow velocities. It is a further object of the presently disclosed subject matter to provide methods that have improved sensitivity over DOCT for small vessels at the resolution limit of the imaging system.

Some of the objects of the subject matter disclosed herein having been stated hereinabove, and which are achieved in whole or in part by the presently disclosed subject matter, other objects will become evident as the description proceeds when taken in connection with the accompanying drawings as best described hereinbelow.

BRIEF DESCRIPTION OF THE DRAWINGS

The patent or application file contains at least one drawing executed in color. Copies of this patent with color drawings(s) will be provided by the Patent and Trademark Office upon request and payment of necessary fee.

The features and advantages of the present subject matter will be more readily understood from the following detailed description which should be read in conjunction with the accompanying drawings that are given merely by way of explanatory and non-limiting example, and in which:

FIGS. 8(a) through 8(g) illustrate SPFI measured flow velocities of a flow phantom according to one embodiment of the presently-disclosed subject matter;

DETAILED DESCRIPTION

Figure 1A:
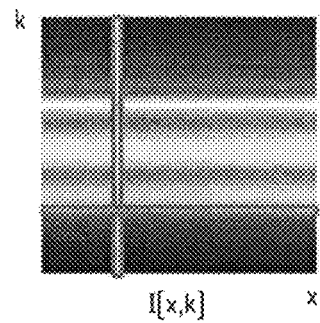
FIGS. 1(a) through 1(e) illustrate steps in a flow chart of conventional SDOCT spectral datacube processing.

The present subject matter provides an improvement on 3D optical angiography. Single-pass volumetric bidirectional blood flow imaging (SPFI) SDOCT detects moving scatterers using a modified Hilbert transform without the use of spatial frequency modulation. Since no frequency modulations are required and SPFI processing is applied to the spatial frequency content across a single B-scan, SPFI is applicable for both spectrometer-based and swept-source OCT systems, provided they have comparable B-scan acquisition rates. Unlike previously described techniques, which require two separate B-scans to detect positive and negative flow, each with modulations tuned to the desired flow direction, SPFI is able to resolve bidirectional flow in a single B-scan pass across the sample.

Detailed Methodology

The depth-encoded complex spectral interferometric signal from M discrete sample reflectors for an SDOCT system can be written as follows:

$$s[k, x] = \sum_{m=1}^{M} A_m \exp[i(2nk\Delta z_m + \theta_h[x] + \theta_m[x])] \quad (1)$$

where k is the wavenumber and $A_m$, $\Delta z_m$, and n represent the reflectivity, depth, and refractive index of each reflector, respectively. Further, $\theta_m$ is a spatially-varying phase term related to the Doppler frequency-shift of the axial component of scatterer motion measured relative to the first lateral A-scan across each scatterer. $\theta_h[x]$ represents the sum of phases arising from an optically heterogeneous sample and can be represented as a random variable with a mean of zero and a standard deviation ($\rho_h[x]$) that is related to the sampling spot-size. Previous work has demonstrated in vivo 3D blood flow mapping by imposing a known axial phase component across a lateral scanning dimension (B-scan) using a moving reference arm. Similarly, modulation of this phase component has also been used for full range complex conjugate resolved SDOCT reconstruction. SPFI-SDOCT is a modification of these previous techniques where scatterers moving above a threshold velocity are imaged without the use of a modulation frequency.

Figure 1B:
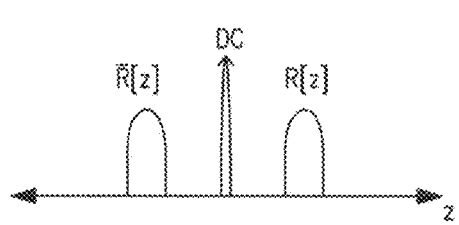
Figure 1C:
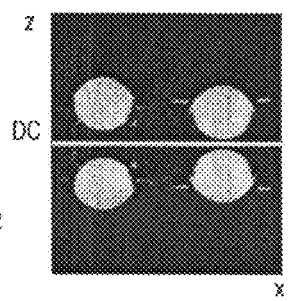

The recorded interferometric signal represents the real-part of a summation of signals from M discrete reflectors (Eq. (1)) in a coherence volume (i.e. spot-size×coherence-length) and thus the phase term ($\theta_m[x]$) can be represented as follows:

$$\theta_m[x] = 2nk\Pi_{w_o/2}\left[x - \frac{dL}{D}\right]\frac{v_m}{v_x}\left(x - \frac{dL}{D} + \frac{w_o}{2}\right) \quad (2)$$

where $v_m$ and $v_x$ are the axial components of scatterer velocities and lateral scan speed, respectively. $\pi$ is the boxcar function defined by $\Pi_{w_o/2}[x-dL/D]=H[x-dL/D+w_o/2]-H[x-dL/D-w_o/2]$ and restricts the measured phase to moving scatterers within the spot-size, $w_o$. d represents the A-scan location of the moving scatterer across a lateral scan of length L, sampled with a density of D A-scans. Combining Eq. (1) and Eq. (2), the sampled interferometric signal can be represented as the conventional SDOCT signal with a velocity-associated phase modulation:

$$s[k,x] = \sum_{m=1}^{M} A_m \exp[i2nk\Delta z_m] \exp[i\theta_h[x]] \exp \quad (3)$$
$$\left[2ink\Pi w_o / 2 \left[x - \frac{dL}{D}\right] \frac{v_m}{v_x} \left(x - \frac{dL}{D} + \frac{w_o}{2}\right)\right]$$
$$= \sum_{m=1}^{M} A_m \exp[i2nk\Delta z_m] g[x] h[x]$$

where g[x] and h[x] are the interferometric components associated with the optical heterogeneity and moving scatterers, respectively. The recorded spectral datacube (I[k,x,y]) in SDOCT is comprised of the real-parts of the interferometric signals (Eq. (3)) accumulated during a 2D raster scan and can be separated into a series of B-scan (I[k, x]) data slices. For instance, FIG. 1(a) illustrates a spectral inverse Fourier transform of a B-scan. The inverse Fourier transform in the spectral dimension, $FT^{-1}_{k \to z}[I[k,x]] = R[z,x] + \overline{R}[z,x]$, represents the depth-resolved reflectivity map in conventional SDOCT. An example of a conventional SDOCT depth-resolved reflectivity map and lateral Fourier transform yields are shown in FIGS. 1(b) and 1(c). Fourier transforming the lateral dimension (i.e., B-scan) yields the spatial frequency content:

$$FT_{x \to u}[I[k,x]] = \sum_{m=1}^{M} A_m \cos[2nk\Delta z_m] \otimes \text{Re}[G[u]] \otimes \text{Re}[H[u]] \quad (4)$$

Figure 1D:
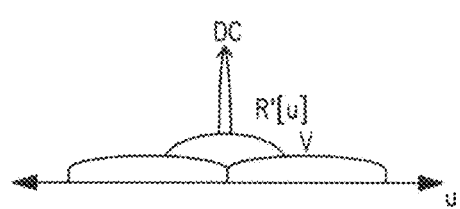
Figure 1E:
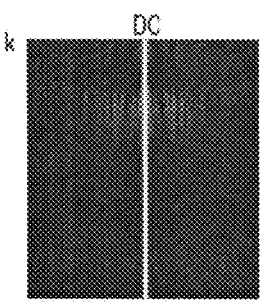

H[u] is the spatial frequency content of the phase associated with moving scatterers integrated across a spot size $$\text{Re}[H[u]] = \text{Re}\left[\int_{dL/D-w_0/2}^{dL/D+w_0/2} \exp\left[2ink\frac{v_m}{v_x}\right] \left(x - \frac{dL}{D} + \frac{w_o}{2}\right) \exp[-iux]dx\right] \quad (5)$$
$$= \kappa \frac{\cos\left[w_0\left(u - 2nk\frac{v_m}{v_x}\right)\right] - 1}{u - 2nk\frac{v_m}{v_x}}$$

where κ is a constant scaling factor. Eq. (4) can be represented in the form of $FT_{x \to z}[I[k,x]] = R'[u,k] + \overline{R}'[u,k] + V_\pm[k,u+f_{D,\pm}]$. Here both moving ($V_\pm[k,u+f_{D,\pm}]$) and non-moving (R'[u,k]) scatterers in the sample are imaged (See, e.g., sample spatial frequency information in FIGS. 1(d) and 1(e)), where $f_{D,\pm}$ represents the Doppler frequency shift associated with the axial components of positive and negative scatterer motion. Note that all scatterer motion and associated flow refer to the axial components of motion (e.g. negative flow refers to the axial components of velocity for scatterers moving away from the sample beam). The Doppler frequency shift is related to Eqs. (2) and (3) by $f_D = nkv_m/\pi$ and can be considered a sum of frequency shifts, representing all moving scatterers within a coherence volume, convolved with their respective reflectivities, in the spatial Fourier domain. Non-moving scatterers, in this case, are centered around DC (See, e.g., FIGS. 1(d) and 1(e)). The spatial frequency bandwidths of both moving and non-moving scatterers across a B-scan are related to the spatial frequency standard deviation of the heterogeneity term (G[u]), where the standard deviation results from a summation of independent random variables:

$$\sigma_h[u] = \sqrt{\sum_{x=1}^{L} \sigma_h^2[x]} \quad (6)$$

and is representative of the spatial correlation between sequentially sampled A-scans with a high correlation lower limit associated with the optical heterogeneity of scatterers within a coherence volume ($\theta_h[x]$) and a Nyquist sampling upper limit.

Figure 2A:
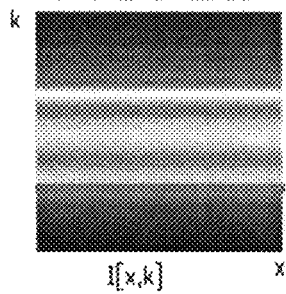
FIGS. 2(a) through 2(f) illustrate steps in a flow chart of SPFI-SDOCT processing according to an embodiment of the presently disclosed subject matter.
Figure 2D:
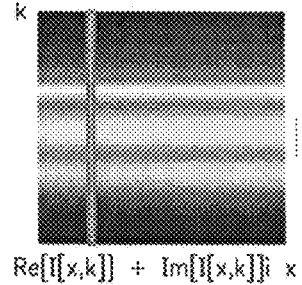
Figure 2E:
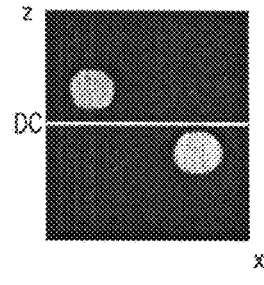
Figure 2B:
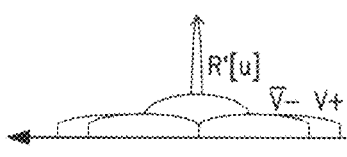
Figure 2C:
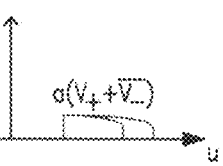

Since the recorded spectral datacube is real-valued, the previously described spatial Fourier transforms include both real and complex conjugate peaks. Previous works have shown that by imposing a constant phase shift between A-scans along a single lateral scan direction, a carrier frequency can be added to the phase term and thus isolating real and complex conjugate peaks to opposite spatial frequency spaces. Windowing out the conjugate peaks, inverse transforming back to k-space (e.g., using a Hilbert transform), and then applying conventional spectral Fourier transforms on the data allowed for separation of moving (e.g., flow) and non-moving (e.g., structure) scatterers to opposite image half-planes. Imaging of bidirectional flow required applying positive and negative carrier frequencies and processing each datacube separately. In SPFI-SDOCT, we recognize that without the use of carrier frequencies, the spatial frequencies of moving and non-moving scatterers do not overlap at spatial frequencies above the non-moving scatterer bandwidth. For instance, FIGS. 2(a) and 2(b) illustrate that a lateral Fourier transform of a B-scan yields a spatial frequency of a sample centered around DC and a spatial frequency of moving scatterers shifted by their respective Doppler frequencies. An analytic signal for the spectral interferogram can be obtained by applying a Heaviside function ($H[u-f_T]$), frequency-shifted outside of the structural bandwidth (See, e.g., FIG. 2(c)), and then inverse Fourier transforming the result (See, e.g., FIG. 2(d)). Application of this modified Hilbert transform (HT*) enables bidirectional flow imaging by windowing Eq. (4) to yield the following:

$$FT_{x \to u}[I[k,x]] \xrightarrow{H[u-f_T]} = \alpha(V_+[k, u+f_{D,+}] + \overline{V}_-[k, u-f_{D,-}]) \quad (7)$$

where α represents the fractional portion of bidirectional flow with Doppler frequencies outside of the spatial frequency bandwidth of non-moving scatterers (See, e.g., FIG. 2(c)). This threshold frequency ($f_T$) defines the minimum detectable velocity in SPFI-SDOCT and is related to the spatial correlation of sequential A-scans. Therefore, lateral oversampling of A-scans allows for a reduced threshold frequency and thus, slower minimum detectable velocities. All spatial frequencies above $f_T$ can be detected given that their associated accumulated phases are above the system phase-noise floor.

Spatial oversampling and velocity resolution can be related by combing the velocity-related Doppler frequency shift with the spatial frequency resolution, which can be represented as follows:

$$dv = \frac{L\lambda_0}{2nD\tau w_o \cos\theta_D} \quad (8)$$

where $\lambda_0$ is the center wavelength, $\tau$ is the integration time, and $\theta_D$ is the Doppler angle between the scanning beam and the direction of scatterer motion. Further, n is the index of refraction, L is the lateral scan length, D is the number of A-scans acquired across the lateral scan, and $w_o$ is the scanning beam spot size. Eq. (8) shows that velocity resolution in SPFI increases and the maximum detectable velocity decreases linearly with increased spatial oversampling.

Figure 2F:
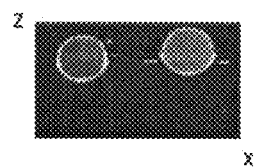

Since the resulting complex interferometric signal is a sum of positive moving scatterers and the conjugate of negative moving scatterers, application of conventional SDOCT processing yields a flow image where bidirectional flow is imaged to opposite sides of DC. For instance, FIG. 2(e) shows a spectral inverse Fourier transform of the analytic interferometric signal maps depth-solved reflectivities of bidirectionally-moving scatterers on opposite image half-planes which can then be overlaid for vessel identification (See, e.g., FIG. 2(f)). Finally, application of the Heaviside function to isolate moving scatterers also acts to reduce the overall noise of the velocity map. It is noted that in a similar analysis for complex conjugate removal, it can be demonstrated that spatial frequency windowing provides an SNR gain related to the window function. Similarly in SPFI, the resulting vessel map should benefit from a signal gain as a result of rejection of noise components outside of the velocity detection band.

In addition, since velocity depends linearly on frequency, application of a spatial frequency window will necessarily filter out all velocities not traveling at velocities described by the following:

$$\Delta v = \frac{L\lambda_0 W[u]}{nD\tau \cos\theta_D} \quad (9)$$

Here, W[u] represents the spatial frequency FWHM bandwidth of the Gaussian window. There is, however, a tradeoff between the spatial frequency window width and the resulting spatial resolution of the velocity-resolved intensity image. For a Gaussian window in frequency-space, the resulting spatially resolved vessel map will be convolved with a Gaussian in the B-scan dimension with FWHM bandwidth $W[x]=4\ln 2/(\pi W[u])$. Thus, to avoid loss of lateral resolution in the velocity-resolved vessel maps, the spatial frequency window bandwidth (W[u]) needs to be constrained such that the associated lateral blurring function (W[x]) does not exceed the scanning beam spot size, $w_o$. The velocity window limit can be represented as the bandwidth $W[u] \geq 4 \ln 2/(\pi w_o)$. Given the discrete sampling parameters of SPFI-SDOCT, the minimum W[u] before loss of resolution is a factor of $8 \ln 2/\pi$ greater than the spatial frequency sampling rate. Combining this result with Eq. (8) gives the minimum resolvable velocity resolution as follows:

$$dv = \frac{4\ln 2 L\lambda_0}{\pi nD\tau w_o \cos\theta_D} \quad (10)$$

Figure 3A:
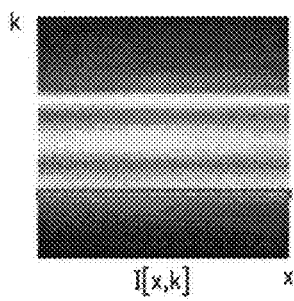
FIGS. 3(a) through 3(e) illustrate steps in a flow chart of velocity-resolved SPFI-SDOCT signal processing according to another embodiment of the presently disclosed subject matter.
Figure 3D:
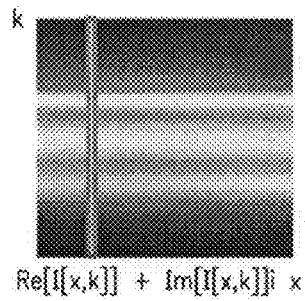
Figure 3E:
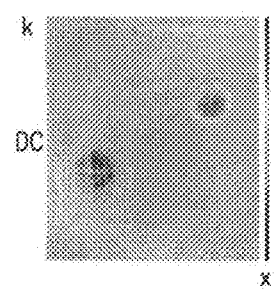
Figure 3B:
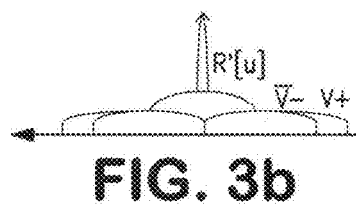
Figure 3C:
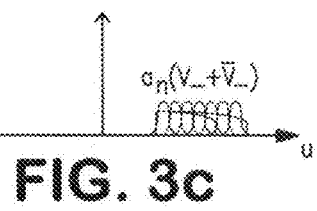

Finally, a datacube (l[x,z,v]) for each B-scan can be formed by shifting the spatial frequency window across the bandwidth of moving scatterers, inverse transforming the result back to functions of l[k,x], and then performing a spectral inverse Fourier transform. For instance, FIGS. 3(a) and 3(b) illustrate that a lateral Fourier transform of raw SDOCT spectral interferogram B-scan (See FIG. 3(a)) yields a spatial frequency of stationary scatterers centered around DC, and spatial frequency of moving scatterers shifted by their respective Doppler frequencies (See FIG. 3(b)). Applying a frequency-shifted Heaviside step function, spatial frequency windowing, and inverse Fourier transforming each frequency range (See FIG. 3(c)) recreates the analytic interferometric signal (See FIG. 3(d)). A spectral inverse Fourier transform of the analytic interferometric signal maps depth-solved reflectivities of moving scatterers for each corresponding velocity range into a datacube for each B-scan (See FIG. 3(e)). Bidirectional flow is mapped onto opposite image half-planes. Summing the datacube across all velocity ranges creates velocity- and depth-resolved B-scans.

Each v-slice represents a velocity range given by Eq. (9), and the datacube can be summed across the v-dimension to create a single velocity-resolved B-scan. Similar to conventional DOCT, velocity wrapping occurs as the spatial frequency content of moving scatterers wraps across the Nyquist sampling upper limit. In this case, the scatterers are mapped to the opposite image half-plane and are therefore represented as moving in the opposite direction. Phase unwrapping techniques, similar to those used for DOCT, can be applied for a singly wrapped velocity profile. Higher spatial frequencies that wrap across Nyquist and have components greater than the threshold frequency ($f_T$) will necessarily lose their velocity components due to SPFI windowing. This fundamentally limits the resolvable spatial frequency range to twice the Nyquist frequency.

Figure 4:
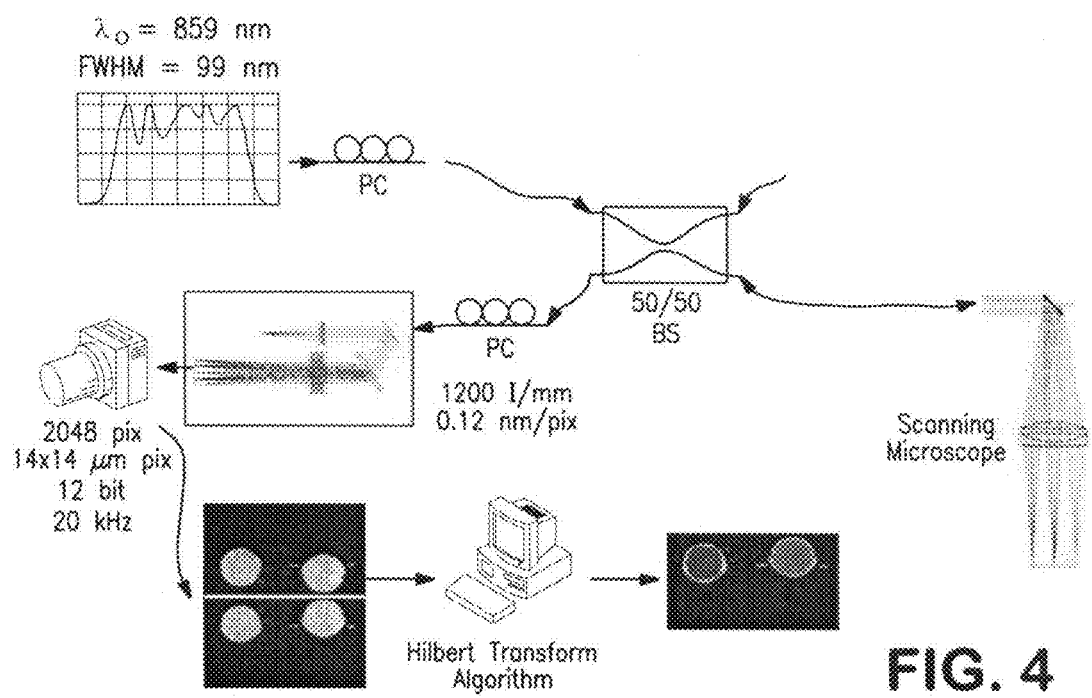
FIG. 4 is a schematic diagram of a SPFI-SDOCT microscope according to one embodiment of the presently-disclosed subject matter.

By way of specific example, SPFI-SDOCT can implemented on a high-speed SDOCT microscope having a specific central wavelength (e.g., at about 859 nm) and a FWHM bandwidth (e.g., about 99 nm), an arrangement for which is shown in FIG. 4. The sample arm can be a microscope (e.g., a custom-built f/8.5 microscope) equipped with scanning galvanometers and imaging optics optimized for a given spot-size (e.g., about 9 μm). SPFI data can be created using both conventional and common path SDOCT configurations by blocking the reference arm of a typical SDOCT interferometer to implement a self-referenced imaging scheme to reduce phase-noise such that $f_T$ is dominated by lateral sampling. Phase-noise between sequential A-scans in a homogeneous phantom can be measured in both conventional and common path configurations. Since the lower limit of the resolving power in SPFI is proportional to the phase-noise, the common path configuration can be used for animal model imaging. Interferometric signals can be captured using a line-scan camera (e.g., a 2048 pixel line-scan camera from e2v, Ltd.). Real-time data acquisition, processing, archiving, and display can be performed, for instance by using a software product (e.g., a custom software program from Bioptigen, Inc.). For example, using a 1.3 mW sample beam, the SNR measured near DC can be 108 dB with an axial resolution of 3.29 μm in tissue and a 6 dB falloff at 0.8 mm. DC removal, k-space resampling, and flow imaging using the modified Hilbert transform algorithm can further be computed during post-processing (e.g., using Matlab from MathWorks, Inc.). In addition, vessel and structure can be visualized (e.g., using Amira from Visage Imaging, Inc.).

Figure 5:
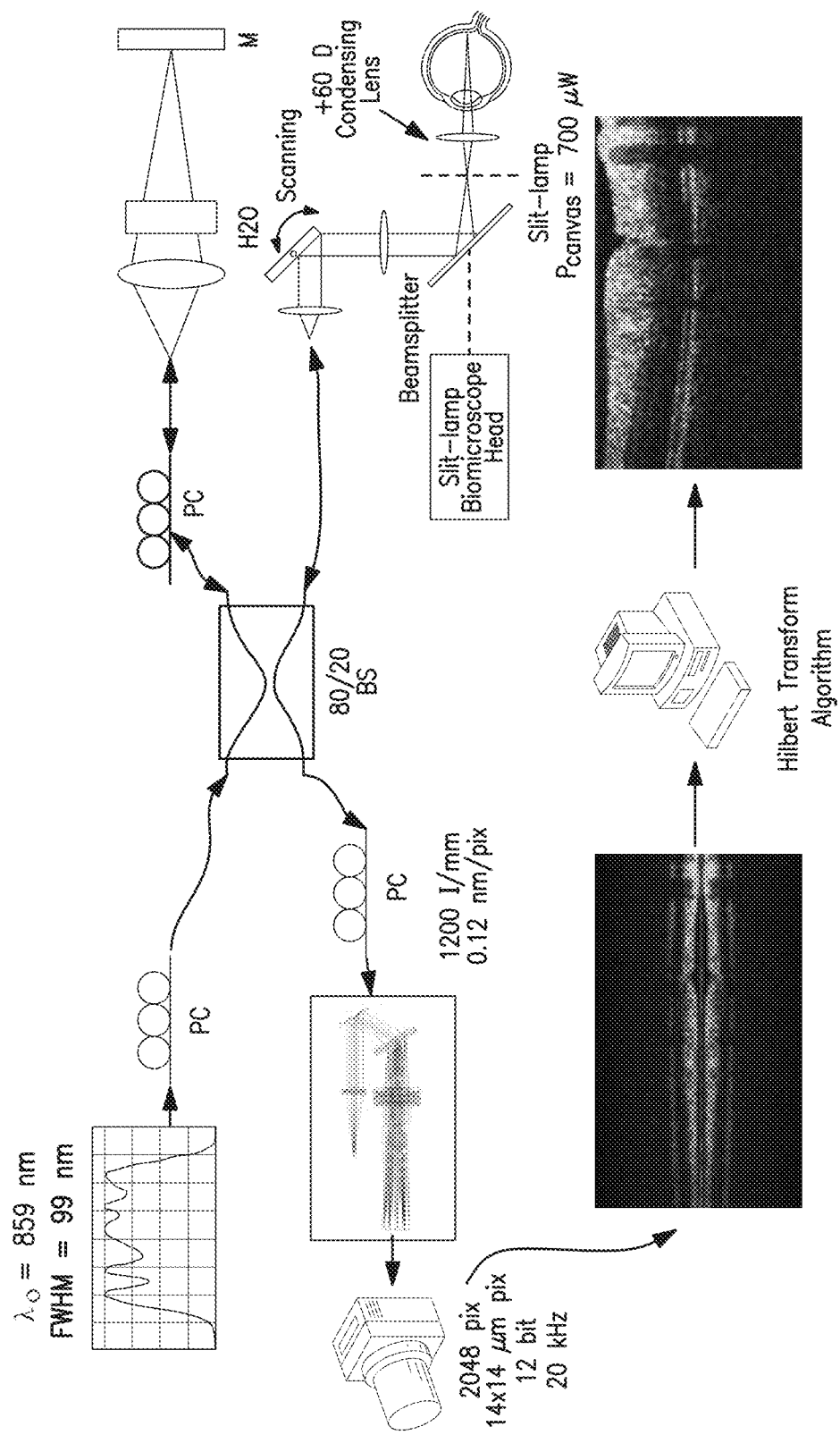
FIG. 5 is a schematic diagram of a SPFI-SDOCT microscope according to another embodiment of the presently-disclosed subject matter.

In another aspect, the disclosed methods can be specifically applied to retinal microvessel imaging. Velocity-resolved SPFI-SDOCT can be implemented on a high-speed SDOCT retinal imaging system employing a light source with a given central wavelength (e.g., about 859 nm) and a given FWHM bandwidth (e.g., about 99 nm), an arrangement for which is illustrated in FIG. 5. The sample arm can be a modified slit lamp equipped with scanning galvanometers and relay optics for retinal imaging of subjects. The retinal scanner optics can be designed for a particular transverse resolution (e.g., about 15-20 µm), as limited by the optics of the eye, across a field (e.g., about 12×12 mm). The reference arm can be dispersion compensated using a water cell and matched optics, and interferometric signals can be captured using a line-scan camera (e.g., a 2048 pixel line-scan camera from e2v, Ltd.). Data acquisition, archiving, and real-time processing and display of image magnitude can be performed, such as by a custom software program. In particular, using a 700 µW sample beam, the SNR measured near DC can be 110 dB with an axial resolution of 4.72 µm in tissue and a 6 dB falloff at 0.8 mm. DC removal, k-space resampling, and flow imaging using the modified Hilbert transform algorithm can be computed during post-processing (e.g., by using Matlab). Vessels and structure can be visualized (e.g., using Amira and OSA ISP from Kitware, Inc.).

Figure 6:
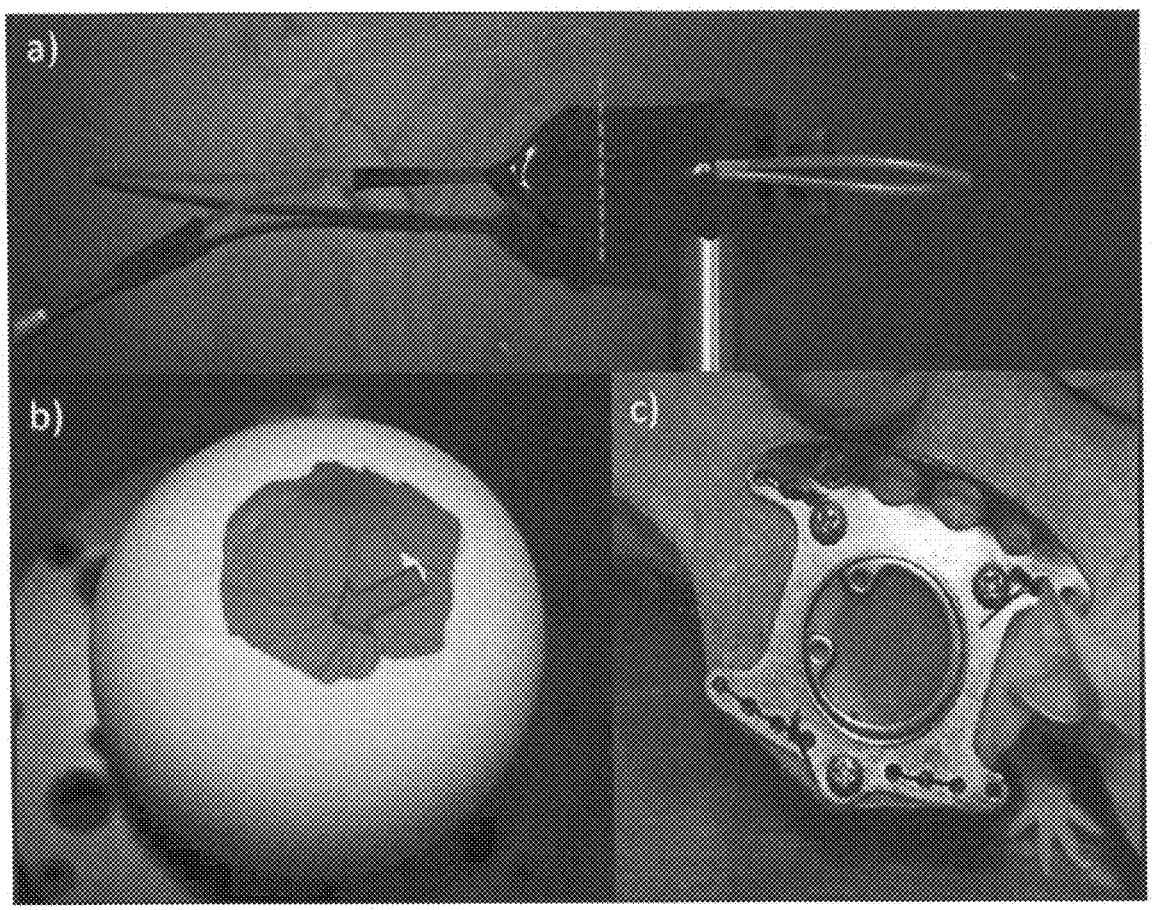
FIGS. 6(a) through 6(c) illustrate examples of SPFI-SDOCT Phantom and in vivo flow models that can be used with the methods of the presently-disclosed subject matter.

Further, velocity-resolved bidirectional flow imaging can be validated and compared with conventional DOCT on a flow phantom (See, e.g., FIG. 6($a$)). In particular, two glass micro-capillary tubes (e.g., 1.5 mm outer diameter, 0.6 mm inner diameter) can be connected using silastic tubing to a syringe pump and pumped with 1% liposyn at one or more of 10 µL/min, 20 µL/min, 30 µL/min, and 40 µL/min. The microcapillaries can then be positioned adjacent to each other on an angled stage such that fluid in the tubes flows in opposite directions in a B-scan cross-section, as is shown in FIGS. 7($a$) through 7($c$), simulating bidirectional flow.

A standard minimum B-scan size of 1000 A-scans/frame for a 3 mm lateral scan at an integration time of 50 µs is assumed. Faster lateral scan velocities can result in galvanometer jitter, and therefore poor image quality and phase stability. Spatial oversampling for SPFI is defined based on these scan parameters in the following. A 3 mm B-scan can be acquired with 1800 A-scans/frame with an A-scan integration period of 50 µs, a factor of 1.8 increase in lateral oversampling. Conventional SDOCT processing (See, e.g., FIG. 7($a$)) can show depth-ranged reflectivity of scatterers including structure, flow, and their complex conjugate mirror images. The directionality of flow in each tube is not readily discernable using conventional processing steps (FIG. 7($a$), arrows 71 and 72). After applying the modified Hilbert transform algorithm, all non-moving scatterer reflectivities (i.e., structure) and mirror images of flow can be resolved leaving only positive and negative flow on opposite image half-planes (See, e.g., FIG. 7($b$)). The phantom structural heterogeneity can be band-limited as a result of lateral oversampling, allowing the frequency-shifted Heaviside function to window out only moving scatterers (Eq. (6)).

Figure 7:
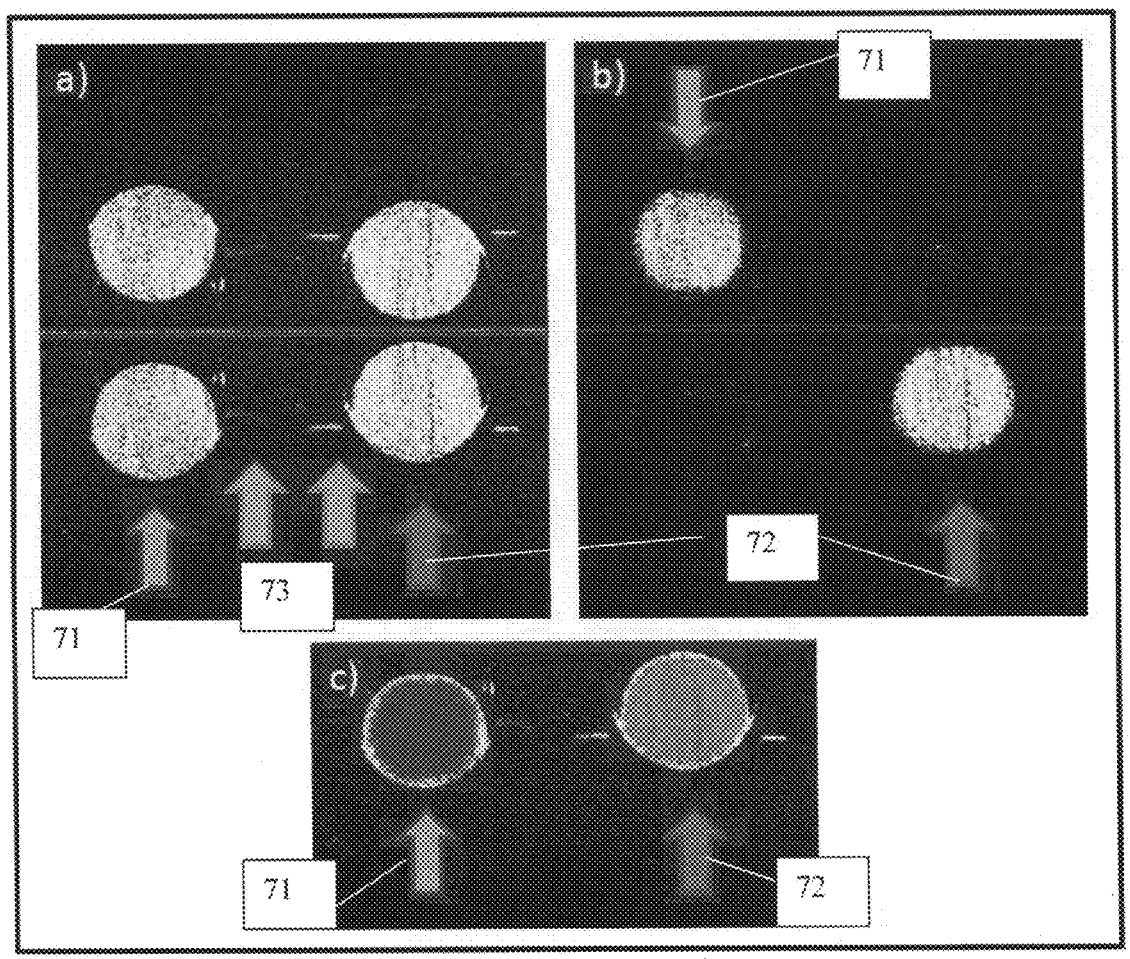
FIGS. 7(a) through 7(c) illustrate flow phantom imaging of both conventional SDOCT depth images and SPFI processed flow images according to one embodiment of the presently-disclosed subject matter.

Similarly, the mirror images of moving scatterers can also be eliminated by application of the modified Hilbert transform, leaving only the real-valued positive flow and complex conjugate negative flow, which can be imaged to opposite sides of DC (See, e.g., FIG. 7($b$)). Using the SPFI processed image, positive and negative flow are separated and overlaid onto the structural image for visualization (See, e.g., FIG. 7($c$)). Given the oversampling parameters and the threshold frequency determined experimentally from the phantom data, the magnitude of the detectable positive and negative flow velocities can be about 0.39-1.12 mm/s.

In another exemplary arrangement, B-scans of the phantom can be acquired across a 2 mm scan range with 2500 A-scans/frame for SPFI and 1000 A-scans/frame with 4 sequential A-scans at each lateral position for DOCT. The SPFI dataset can be laterally oversampled compared to DOCT because velocity resolution increases as a function of spot-size overlap on the sample (Eq. (8)). Both datasets can be acquired with an integration time of 50 µs. At these sampling parameters, the total imaging time for SPFI can be a factor of 1.6 times faster than that of DOCT. SPFI parameters can be chosen to demonstrate velocity resolution at the lower limit of the detection range for a given integration time as a comparison with DOCT. Since the velocity resolution of DOCT is limited by the phase noise of the system instead of spatial sampling parameters, as is the case with SPFI, an appropriate lateral spacing can be used to minimize scanner jitter. The number of sequential A-scans used can be indicative of common DOCT sampling parameters.

Figure 8A:
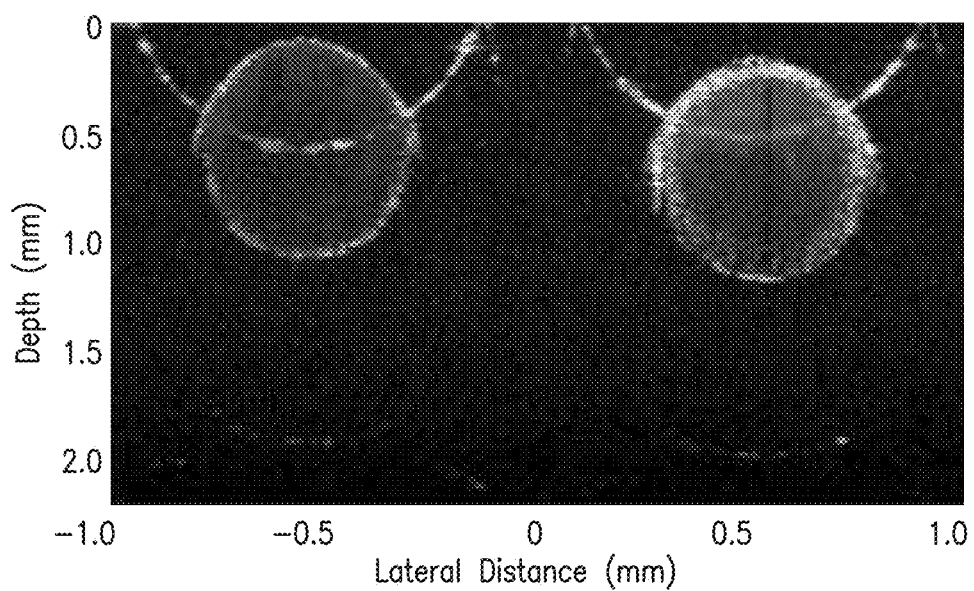

In addition, a threshold frequency can be determined, which can filter out all spatial frequencies of non-moving scatterers. A Gaussian window can then be moved across the remaining spatial frequencies to velocity-resolve the B-scan for flow rate measurements. The shifted window can be set such that the velocity-range resolved has a FWHM and shifts at increments of 24.3 µm/s. Given the oversampling parameters and threshold frequency window used, the magnitude of the total detectable velocity range for the axial components of positive and negative velocities can be about 0.61-11.53 mm/s. Velocity-resolved scatterer information can then be overlaid onto structural B-scans for visualization (See, e.g., FIG. 8($a$)). DOCT volumes can be processed using standard phase-difference methods. Velocity profiles for both DOCT (See, e.g., FIGS. 8($b$) and 8($c$)) and SPFI (See, e.g., FIGS. 8($d$) and 8($e$)) can be fit to laminar flow curves, and measured capillary cross-section and flow rate can be calculated for both imaging methods and compared (See, e.g., FIGS. 8($f$) and 8($g$)).

Vessel imaging can also be demonstrated on chicken embryo and mouse tumor window chamber models (See, e.g., FIGS. 6($b$) and 6($c$)). In particular, fertilized Hubert Ross chicken eggs can be incubated at 38° C. and 97% humidity in a forced-draft incubation chamber. A 3 mm×3 mm volume mosaic was created by acquiring nine 1 mm×1 mm volumes imaged with 1800 A-scans/frame and 100 frames/volume, a factor of 5.4 increase in lateral oversampling. At Hamburger-Hamilton (HH)-stages 23-25, a window can be created through the outer shell and the chorionic membrane can be removed. Peripheral yolk vasculature (See, e.g., FIG. 6($b$)) can then be imaged using the commonpath configuration with the top amnion surface as the reference reflector. Vessels away from the embryo can be imaged to avoid pulsatile flow as a result of heart beat. Embryo temperatures can be maintained using a heat-lamp during the course of imaging. Each SPFI-SDOCT reconstructed frame can be separated into two halves and combined to create bidirectional flow maps with intensities corresponding to the reflectivity of scatterers moving into or out of the A-scan axis.

Figure 9:
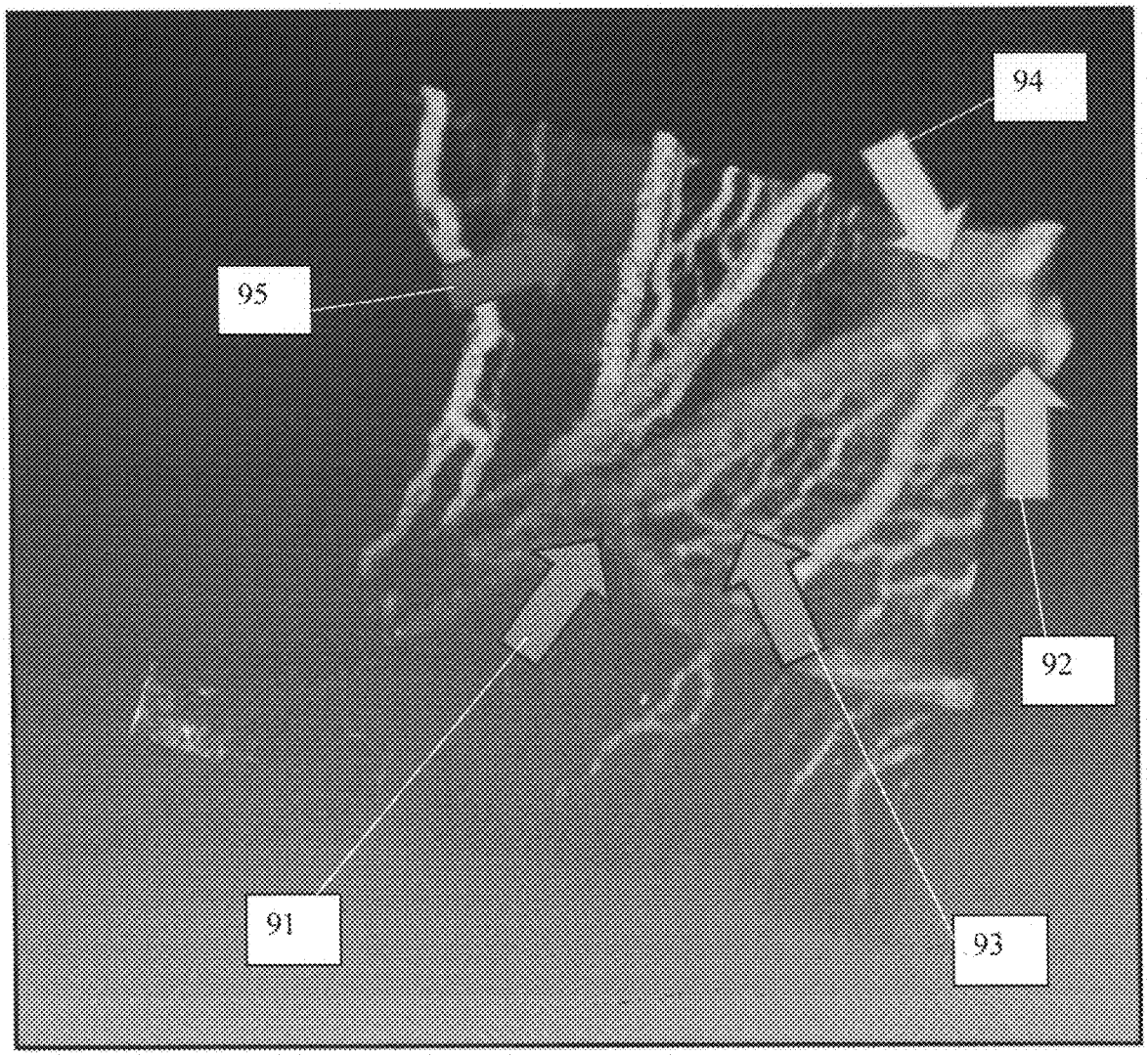
FIGS. 9, 10, and 11 illustrate 3D reconstructions of bidirectional volumetric flow magnitudes in SPFI-SDOCT flow models according to embodiments of the presently-disclosed subject matter.
Figure 10:
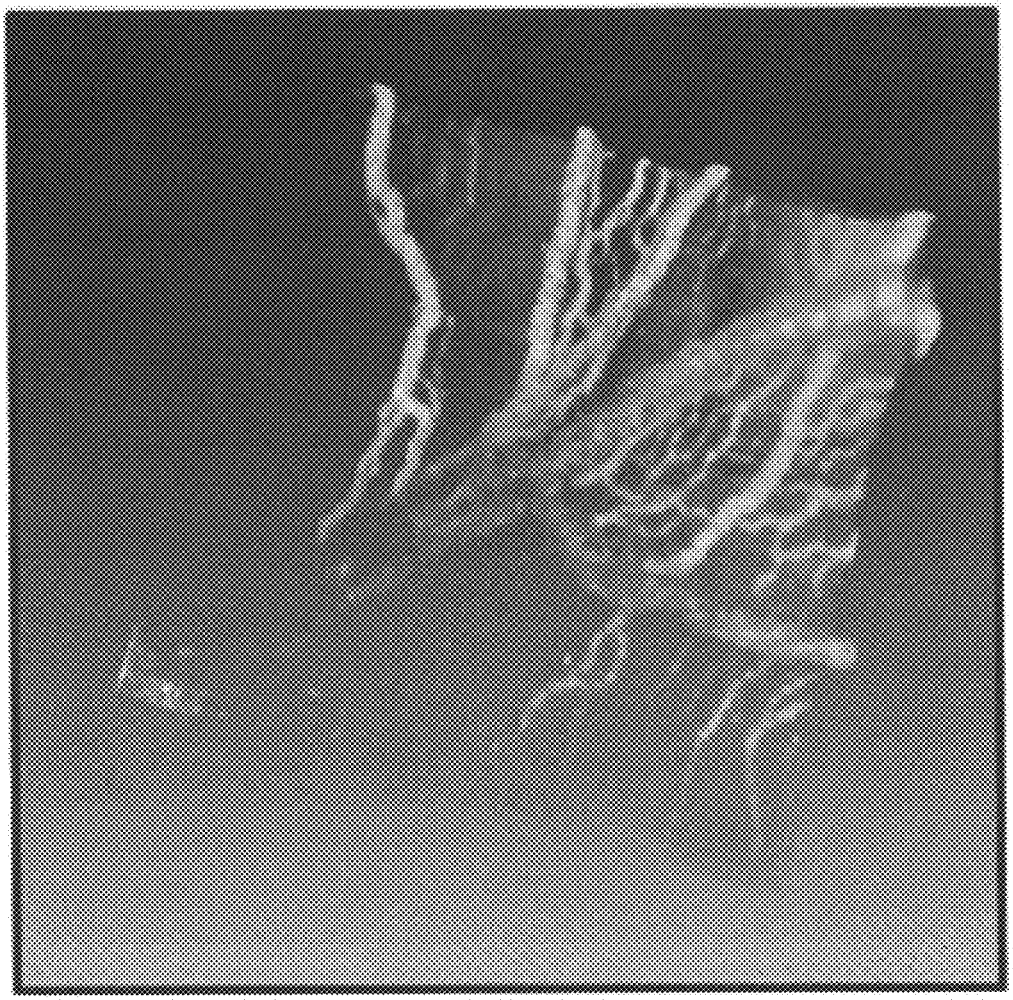

The peripheral yolk vascular network, shown in FIG. 9, is clearly visible in the chicken embryo model. SPFI-SDOCT imaged vessels are tubular, as expected, and appear to be confined to a 500 µm layer (See, e.g., FIG. 10). The large and partially imaged vessel across the volume mosaic (See FIG. 9, arrow 91) is a shadow artifact arising from imaging through a large vessel in the amionic (i.e., the reference reflector) layer. The well defined portion of this vessel (See FIG. 9, arrow 92) represents areas where the vessel branches from the yolk surface up towards the surface of the amnion. The faded regions (See FIG. 9, arrow 91) are areas where the vessel is on top of the amion surface and out of the imaging depth range. Yolk surface vessels follow the curvature of the yolk sac and are shown gradually descending away from the reference surface (See FIG. 10). Detected vessel sizes ranged from 40

μm (FIG. 9, arrow 93) to 270 μm (FIG. 9, arrow 94). "Hazy" sections (FIG. 9, arrow 95) are indicative of sample bulk motion which resulted in non-moving structural scatterers being resolved along with flow. Chicken embryo volumes were acquired using 1 ms A-scan integration time in order to detect small vessels with minimal flow velocities. The magnitude of the detectable positive and negative flow velocities for the embryo model was 65.6-168.6 μm/s.

Figure 11:
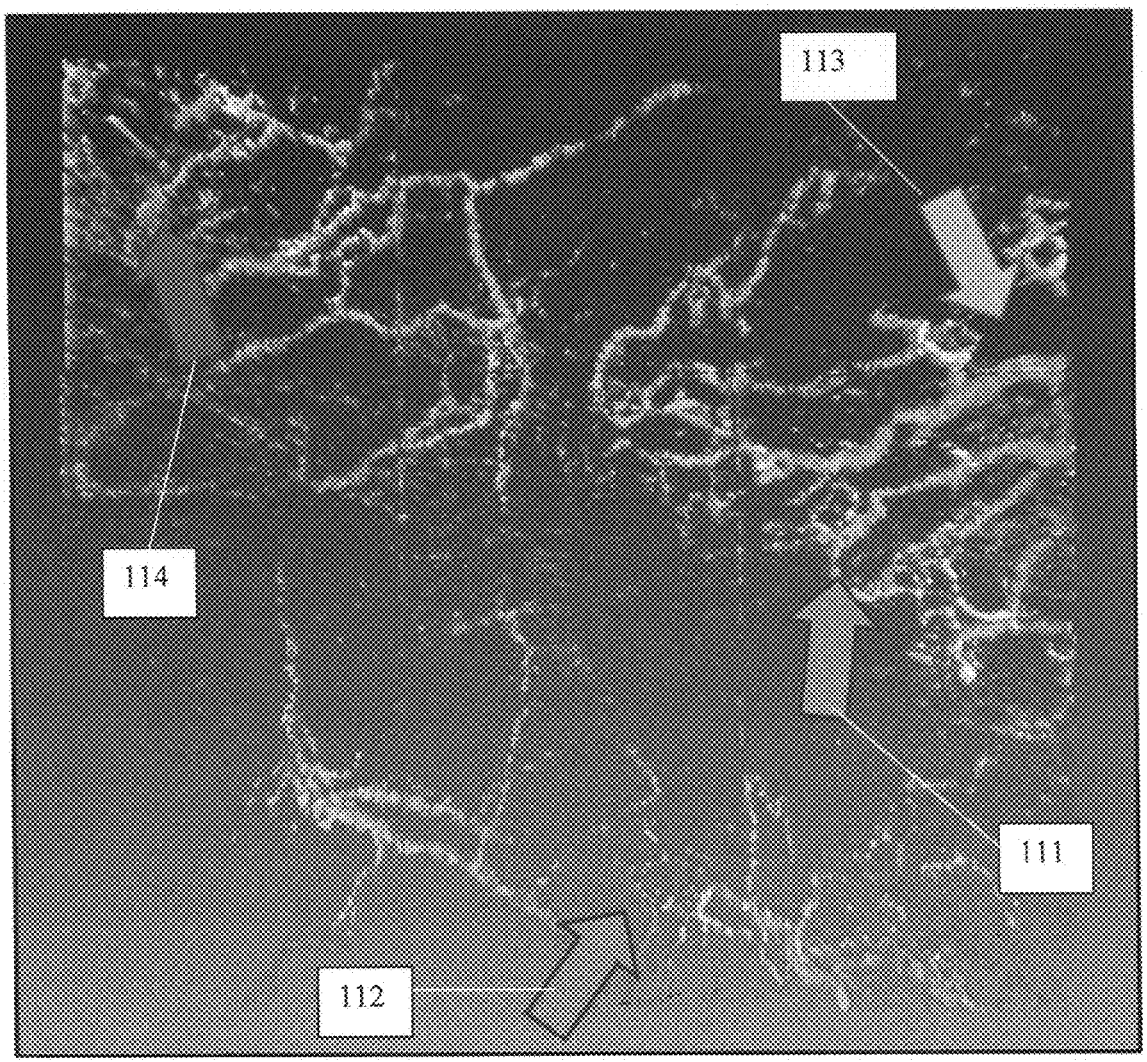

Mouse tumor models can be prepared by surgically implanting a titanium window chamber on the back of anthymic (nu/nu) nude mice under anesthesia (ketamine 100 mg/kg and xylazine 10 mg/kg intraperitoneal). 4T1 metastatic mouse mammary adenocarcinoma cells can be used. During window implantation, 10 μL of a cell suspension of 5 103 cells can be injected into the dorsal skin flap and covered with a 12 mm diameter #2 round glass coverslip over the exposed skin (See, e.g., FIG. 6(c)). Animals can be housed in an environmental chamber with free access to food and water and standard 12 hr light and dark cycles. Mice tumors were imaged two weeks after implantation using the window chamber surface as a reference reflector. Mice can be imaged using the commonpath configuration, self-referenced using the surface of the window chamber as the reference reflector. Tumor regions were indentified prior to imaging (See, e.g., FIG. 11, arrow 111) and show highly tortuous vessels indicative of neoplastic angiogenesis. Surrounding vasculature indicate normal skin fold vessels. Detected vessel sizes ranged from 20 μm (See, e.g., FIG. 11, arrow 112), which approaches the sampling limit of the microscope, to 110 μm (See, e.g., FIG. 11, arrow 113). The volumes were acquired using 2 ms A-scan integration time in order to detect small vessels however these volumes were more sensitive to bulk motion artifacts (See FIG. 8, arrow 114). The magnitude of the detectable positive and negative flow velocities for the mouse tumor model was 32.8-84.3 μm/s. Small noise signals throughout the volumes indicate areas of reference reflector saturation due to small optical reflectivity heterogeneities across the reference window chamber surface.

Figure 12:
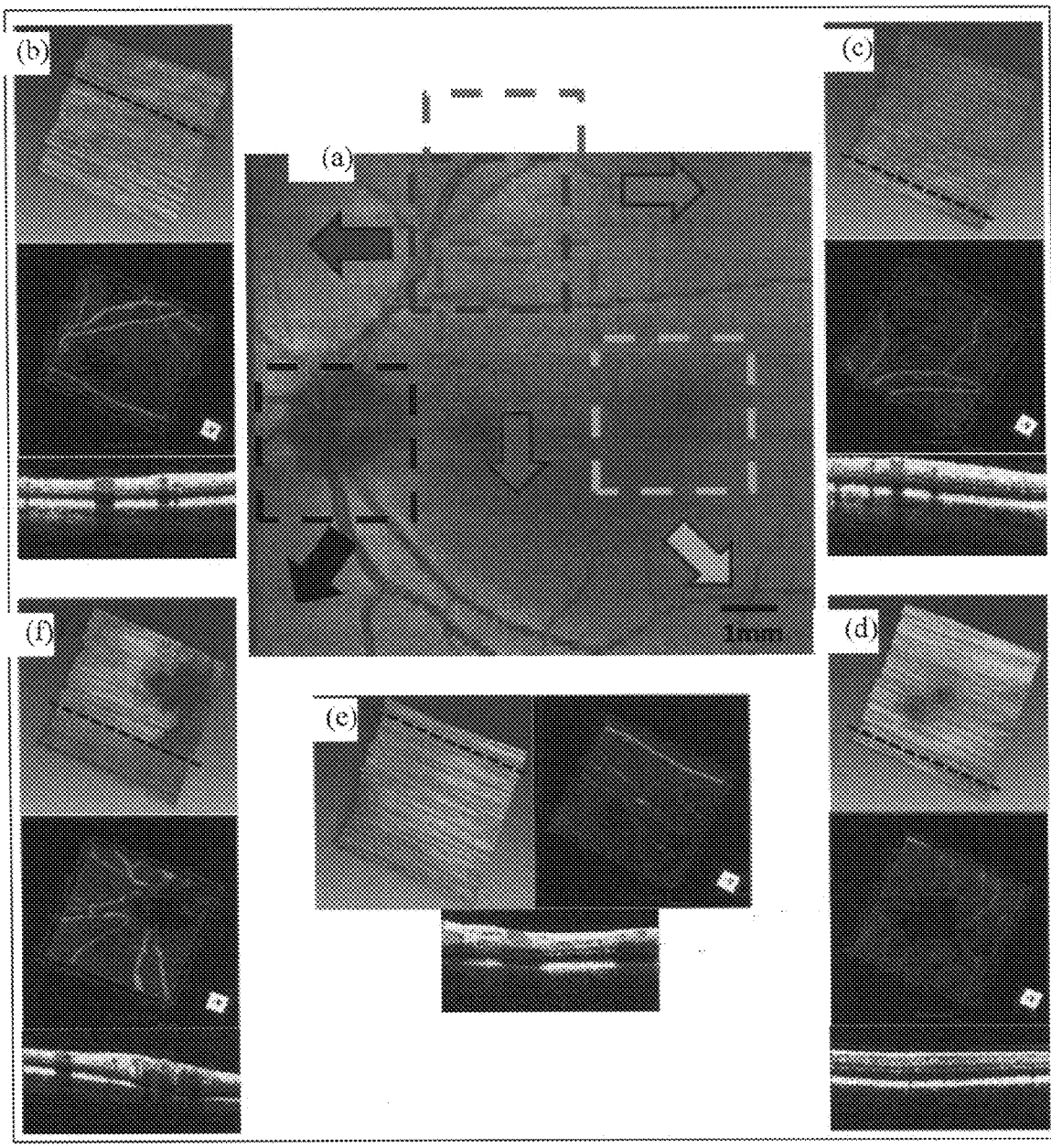
FIGS. 12(a) through 12(f) illustrate volumes of an in vivo human retina at several locations across the macula according to an embodiment of the presently-disclosed subject matter.

In vivo microvessel imaging can further be demonstrated in a normal human retina. First, an OCT volume of the subject (e.g., a 10×10 mm volume) can be acquired, allowing for the reconstruction of a standard OCT summed voxel projection (SVP) to use as an atlas to locate smaller volumes imaged using SPFI, which is shown in FIG. 12(a). Several volumes (e.g., 2×2 mm volumes) can then be densely-sampled using SPFI parameters (e.g., 2500 A-scans/frame; 100 frames/volume; 100 μs integration time, 25 s total imaging time) at several locations across the macula (See, e.g., FIGS. 12(b), 12(b), and 12(e)), including landmarks such as the fovea (See, e.g., FIG. 12(d)) and optic nerve (See, e.g., FIG. 12(f). Given the sampling parameters, threshold frequency, and assuming a 20 μm scanning beam spot-size on the retina, the detectable velocity range for axially moving scatterers can be about 0.45-8.64 mm/s. Parameters can be set for a lower velocity range, compared to flow phantoms, to adequately detect slow flow in small foveal vessels (e.g., <30 mm/s). The frequency window can be set such that the velocity-range has a particular FWHM (e.g., about 18.4 μm/s) and is shifted at specified increments (e.g., about 82.8 μm/s). Bulk motion correction can be implemented prior to SPFI windowing. Velocity-resolved B-scans can be used to determine vascular size by fitting velocity profiles to parabolic flow curves and then calculating the zero-velocity crossing positions. Finally, blood flow rates and total retinal flow can be calculated for a 2×2 mm velocity-resolved volume of human fovea.

It is understood that SPFI acquisition of the entire macula in a single volume dataset would be impractical. Since velocity resolution and lateral sampling density are coupled in SPFI by Eq. (8), an order of magnitude increase in the lateral sampling density (i.e., A-scans/frame) would be required. This requirement can limit the SPFI sampling volume size by both the available memory in the acquisition software and total imaging time.

Figure 13:
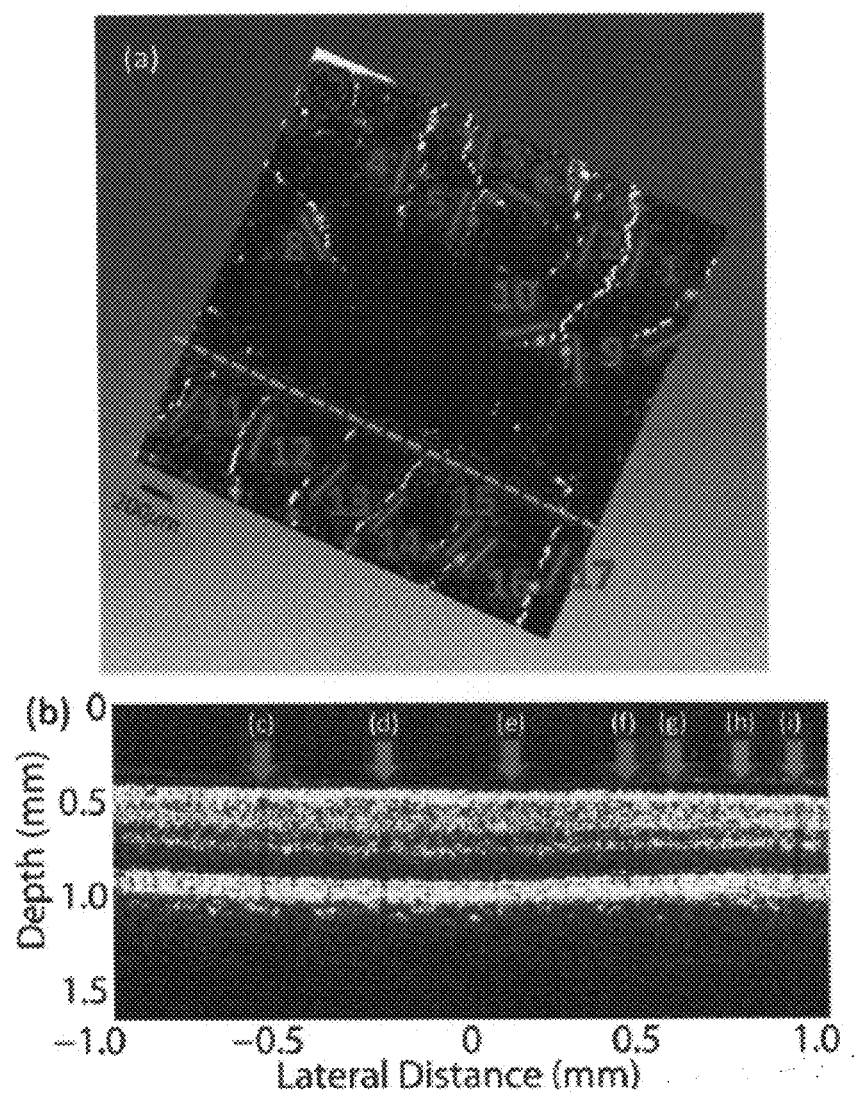
FIGS. 13(a) through 13(i) illustrate a velocity-resolved volumetric flow map of in vivo human fovea and velocity profiles for vessels contained therein according to one embodiment of the presently-disclosed subject matter.

Depth-resolved vessel maps for each volume can be first reconstructed and overlaid onto structural OCT data to distinguish macular vasculature (See FIG. 12(a) through 12(e)). Total blood flow measurements can then be calculated for a single 2×2 mm volume of the fovea (See FIG. 12(c)). The structural OCT data can show the foveal pit and the associated SPFI vascular map can confirm its location by resolving a circular avascular zone surrounded by a set of terminal capillaries. First, the resolved vessels in the volume can be identified as arteries and veins using the flow directionality information calculated by SPFI (See FIG. 13(a)). Vessel orientation and Doppler angle can then be measured for all 17 resolved vessels, and velocity profiles can be measured at a single point for each vessel (See, e.g., FIG. 13(a), dots). Doppler angles can be measured by calculating the vessel cross-section displacement across sequential B-scans in the 3D datasets. The velocity profiles can then be fit to laminar flow curves to determine both the peak velocity and diameter of each vessel. Finally, the vessel size, orientation, and velocity information can be used to calculated the total foveal blood flow. A representative B-scan (See, e.g., FIG. 13(b)) taken across the foveal volume (dotted line in FIG. 13(a)) is shown with velocity-resolved flow content overlaid on top of the structural image. The velocity profiles and parabolic fits for each of the vessels are included (See FIGS. 13(c) through 13(i)) to show the strong correlation between velocities measured using SPFI and their respective laminar flow velocity profiles (mean R2=0.95). Closer inspection of vessel 17 (See FIG. 13(i)) shows a blunted parabolic velocity profile, characteristic of red blood cell aggregation in microvasculature, consistent with rheological observations.

A summary of the size, peak velocity, and flow measurements for all vessels identified in a representative 2×2 mm foveal volume are shown in Table 1 below (veins identified by (*)). In this representative volume, the smallest resolvable vessel was 13.64 μm, which is at the resolution limit of the retinal SDOCT system. The average measured foveal vessel diameter is about 22 μm, and average arterial flow velocity is greater than average venous flow velocity, which is supported by similar measurements made using LDV. The detected velocities range from 5.97-30.22 mm/s, concurrent with human retinal vessels in the corresponding size range, also measured using LDV. Finally, the total arterial and venous flow show a net inflow of blood into the fovea. This can be a result of the presence of unresolved veins in the volume and expected errors from measurements of vessel orientation angle and calculation of diameter, which would significantly impact blood flow calculations.

TABLE 1

| Vessel Number | Diameter (μm) | Peak Velocity (mm/s) | Flow (μL/min) |
| --- | --- | --- | --- |
| 1 | 28.81 | 23.51 | 0.460 |
| 2* | 20.86 | −17.07 | −0.175 |
| 3* | 18.25 | −16.45 | −0.129 |
| 4 | 23.41 | 16.35 | 0.211 |
| 5* | 21.33 | −5.97 | −0.064 |
| 6* | 22.24 | −10.66 | −0.124 |
| 7 | 22.81 | 24.99 | 0.306 |
| 8 | 22.92 | 13.65 | 0.169 |

TABLE 1-continued

| Vessel Number | Diameter (μm) | Peak Velocity (mm/s) | Flow (μL/min) |
|---|---|---|---|
| 9 | 14.49 | 16.76 | 0.083 |
| 10 | 21.84 | 13.55 | 0.152 |
| 11* | 21.52 | −10.62 | −0.116 |
| 12 | 28.64 | 11.34 | 0.219 |
| 13* | 20.36 | −24.41 | −0.239 |
| 14* | 27.05 | −18.87 | −0.325 |
| 15* | 26.93 | −7.88 | −0.135 |
| 16 | 13.64 | 30.22 | 0.133 |
| 17 | 24.85 | 10.87 | 0.158 |

While SPFI allows for velocity-resolved volumetric blood flow imaging with velocity resolution comparable to that of DOCT, there are several differences between the modalities that can be noted. Since velocity resolution and spatial oversampling are coupled, this allows for the flexibility to set sampling parameters to a desired velocity range. This flexibility would allow for improved data acquisition speeds over DOCT for imaging of small spatial volumes of moderately high flow velocities, but could potentially require longer scanning times for large scan areas with low flow. As discussed previously, the velocity resolving power of SPFI falls off at the lower limits of velocity detection, as compared to DOCT, but is comparable for high flow velocities. Since velocity-resolved SPFI requires a sliding spatial frequency window, this increases the number of Fourier transforms required by the number of velocity increments desired. However, this increase in computational complexity is essentially trivial since FFT algorithms can be optimized and the transforms can be parallelized. Finally, it has been shown that spatial frequency filtering results in a sensitivity improvement, which gives SPFI a detection advantage over DOCT for small vessels at the resolution limit of the imaging system. The overall advantage of SPFI over DOCT is in its improved sensitivity and customizability over velocity resolution, velocity range, and acquisition time in exchange for small increases in computational complexity.

The present subject matter can be embodied in other forms without departure from the spirit and essential characteristics thereof. The embodiments described therefore are to be considered in all respects as illustrative and not restrictive. Although the present subject matter has been described in terms of certain preferred embodiments, other embodiments that are apparent to those of ordinary skill in the art are also within the scope of the present subject matter.

What is claimed is:

1. A method for single-pass flow imaging using a spectral domain optical coherence tomographic (SDOCT) device, comprising:
    (a) producing interferometric signals from an SDOCT device, the interferometric signals containing moving scatterer data and non-moving scatterer data;
    (b) separating the moving scatterer data from the non-moving scatterer data in the interferometric signals using a Hilbert transform having a frequency shifted filter function; and
    (c) producing a flow image of the moving scatterer data.

2. The method of claim 1, wherein producing interferometric signals comprises producing a series of A-scans of an object to be imaged and combining the series of A-scans to form a B-scan.

3. The method of claim 2, wherein producing a series of A-scans comprises laterally oversampling of A-scans.

4. The method of claim 1, wherein producing interferometric signals comprises producing interferometric signals from commonpath SDOCT device configurations.

5. The method of claim 1, wherein the moving scatterer data comprises positive and negative flow data, and producing a flow image comprises producing separate positive and negative flow images from the positive and negative flow data.

6. The method of claim 5, further comprising combining the positive and negative flow images to create a bidirectional flow map.

7. The method of claim 5, wherein producing interferometric signals from an SDOCT device comprises producing a series of A-scans of an object to be imaged and combining the series of A-scans to form a single B-scan that contains the moving scatterer data comprising the positive and negative flow data that is used to produce the separate positive and negative flow images.

8. The method of claim 1, wherein producing a flow image comprises producing a velocity-resolved flow image.

9. The method of claim 1, wherein using the Hilbert transform comprises applying a Heaviside function to isolate the moving scatterer data.

10. The method of claim 1, wherein using the Hilbert transform comprises using a Gaussian window to isolate the moving scatterer data.

11. The method of claim 1, wherein using the Hilbert transform comprises:
    applying a lateral Fourier transform to the interferometric signals to yield spatial frequencies of the moving scatterer data and the non-moving scatterer data;
    applying a Heaviside function that is frequency-shifted outside of a structural bandwidth of the spatial frequencies of the moving scatterer data and the non-moving scatterer data to obtain results that include isolated moving scatterer data; and
    applying an inverse Fourier transform to the results of the application of the Heaviside function.

12. The method of claim 1, wherein producing interferometric signals from an SDOCT device comprises producing interferometric signals from an SDOCT device without using a spatial frequency modulation.

13. A method for single-pass blood flow imaging, comprising:
    (a) emitting a light from a light source;
    (b) splitting the light into a first light and a second light;
    (c) directing the first light toward a sample containing moving and non-moving scatterers within a depth to produce a first reflected light, the first reflected light containing an image of both the moving and non-moving scatterers;
    (d) directing the second light toward a reference reflector to create a second reflected light;
    (e) combining the first reflected light and the second reflected light to produce interferometric signals, the interferometric signals containing moving scatterer data and non-moving scatterer data;
    (f) separating the moving scatterer data from the non-moving scatterer data in the interferometric signals using a Hilbert transform having a frequency shifted filter function; and
    (g) producing a flow image of the moving scatterer data that represents blood flow.

14. The method of claim 13, wherein directing the first light toward a sample comprises directing the first light toward a human retina.

15. The method of claim 13, wherein the moving scatterer data comprises positive and negative flow data, and producing a flow image comprises producing separate positive and negative flow images from the positive and negative flow data.

16. The method of claim 15, further comprising combining the positive and negative flow images to create a bidirectional flow map.

17. The method of claim 13, wherein producing a flow image comprises producing a velocity-resolved flow image.

18. The method of claim 13, further comprising determining blood flow rates from the flow image.

19. The method of claim 13, wherein using the Hilbert transform comprises applying a Heaviside function to isolate the moving scatterer data.

20. The method of claim 13, wherein using the Hilbert transform comprises using a Gaussian window to isolate the moving scatterer data.

21. A method for single-pass flow imaging using a spectral domain optical coherence tomographic (SDOCT) device, comprising:
(a) producing interferometric signals from an SDOCT device without using a spatial frequency modulation, the interferometric signals containing moving scatterer data and non-moving scatterer data;
(b) separating the moving scatterer data from the non-moving scatterer data in the interferometric signals using a Hilbert transform having a frequency shifted filter function, where the Hilbert transform determines spatial frequencies of the moving scatterer data and the non-moving scatterer data and filters the spatial frequencies of the non-moving scatterer data to isolate the moving scatterer data; and
(c) producing a flow image of the moving scatterer data.

22. A method for single-pass flow imaging using a spectral domain optical coherence tomographic (SDOCT) device, comprising:
(a) producing interferometric signals from an SDOCT device, the interferometric signals containing moving scatterer data and non-moving scatterer data;
(b) applying a Hilbert transform having a frequency shifted filter function to the interferometric signals to determine spatial frequencies of the moving scatterer data and the non-moving scatterer data and filter the spatial frequencies of the non-moving scatterer data to isolate the moving scatterer data; and
(c) producing a flow image of the moving scatterer data.

* * * * *